(12) United States Patent
Desai et al.

(10) Patent No.: US 9,903,035 B2
(45) Date of Patent: Feb. 27, 2018

(54) DEVICES, SYSTEMS AND METHODS FOR COATING SURFACES

(71) Applicant: The Regents of the University of California, Oakland, CA (US)

(72) Inventors: Tejal A. Desai, San Francisco, CA (US); Harald Nuhn, Palo Alto, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/649,188

(22) PCT Filed: Dec. 2, 2013

(86) PCT No.: PCT/US2013/072603
§ 371 (c)(1),
(2) Date: Jun. 2, 2015

(87) PCT Pub. No.: WO2014/088944
PCT Pub. Date: Jun. 12, 2014

(65) Prior Publication Data
US 2015/0322583 A1      Nov. 12, 2015

Related U.S. Application Data

(60) Provisional application No. 61/732,773, filed on Dec. 3, 2012.

(51) Int. Cl.
C25D 11/04    (2006.01)
C25D 5/02    (2006.01)
(Continued)

(52) U.S. Cl.
CPC .............. *C25D 5/02* (2013.01); *A61L 27/306* (2013.01); *A61L 31/088* (2013.01); *C25D 7/04* (2013.01);
(Continued)

(58) Field of Classification Search
CPC .......... C25D 5/02; C25D 7/04; C25D 11/005; C25D 11/06; C25D 11/16; C25D 11/26;
(Continued)

(56) References Cited

U.S. PATENT DOCUMENTS 3,361,662 A * 1/1968 Sutch ................... C25D 11/005
204/224 R
4,919,771 A 4/1990 Wilkening
(Continued)

FOREIGN PATENT DOCUMENTS

CN       101469437       7/2009
CN       103361702       10/2013
(Continued)

OTHER PUBLICATIONS

Sulka, G.D., "Nanostructured Materials in Electrochemistry", 2008, Ch. 1, p. 1-116.*
(Continued)

*Primary Examiner* — Luan V Van
*Assistant Examiner* — Alexander W Keeling
(74) *Attorney, Agent, or Firm* — Edward J. Baba; Shweta Chandra; Bozicevic, Field & Francis LLP

(57) ABSTRACT

The present disclosure provides devices, systems and methods with applicability in the coating of surfaces, in particular three-dimensional surfaces, via anodization reactions. For example, the disclosed devices, systems and methods find use in the formation of microstructured or nanostructured layers, e.g., metal oxide microstructured or nanostructured layers, via anodization on a variety of devices including, e.g., medical devices. Devices modified with one or more microstructured or nanostructured layers are also provided.

24 Claims, 14 Drawing Sheets

(51) Int. Cl.
*C25D 7/04* (2006.01)
*C25D 11/26* (2006.01)
*C25D 17/06* (2006.01)
*C25D 17/12* (2006.01)
*C25D 11/00* (2006.01)
*A61L 27/30* (2006.01)
*A61L 31/08* (2006.01)

(52) U.S. Cl.
CPC ............ *C25D 11/005* (2013.01); *C25D 11/26* (2013.01); *C25D 17/06* (2013.01); *C25D 17/12* (2013.01); *A61L 2400/12* (2013.01); *A61L 2420/02* (2013.01); *A61L 2430/02* (2013.01)

(58) Field of Classification Search
CPC ........ C25D 17/06; C25D 17/12; C25D 11/02; C25D 17/10
USPC .......................................................... 205/324
See application file for complete search history.

(56) References Cited

U.S. PATENT DOCUMENTS

| | | | | |
|---|---|---|---|---|
| 6,045,677 | A * | 4/2000 | Beetz, Jr. ................ | C25D 11/02 205/122 |
| 6,375,826 | B1 | 4/2002 | Wang et al. | |
| 6,679,980 | B1 | 1/2004 | Andreacchi | |
| 9,315,916 | B2 * | 4/2016 | Hayashi ............... | C25D 17/005 |
| 2007/0209929 | A1 | 9/2007 | Schaeffer et al. | |
| 2007/0209947 | A1 | 9/2007 | Shrivastava et al. | |
| 2007/0222460 | A1 * | 9/2007 | Price ..................... | C25D 11/02 324/644 |
| 2009/0236228 | A1 * | 9/2009 | Yamamoto ............. | C25D 11/04 205/83 |
| 2010/0073995 | A1 | 3/2010 | Tran | |
| 2010/0318193 | A1 | 12/2010 | Desai et al. | |
| 2011/0209990 | A1 * | 9/2011 | Ha ......................... | C25D 11/02 204/196.02 |
| 2011/0218643 | A1 | 9/2011 | Yerokhin | |
| 2012/0114734 | A1 | 5/2012 | Desai et al. | |
| 2012/0171112 | A1 | 7/2012 | Lee et al. | |
| 2013/0319865 | A1 * | 12/2013 | Browning ............... | B23P 11/00 205/50 |
| 2014/0342236 | A1 * | 11/2014 | Goyal .................... | B82Y 10/00 429/245 |

FOREIGN PATENT DOCUMENTS

| | | | | |
|---|---|---|---|---|
| EP | 1222901 | | 7/2002 | |
| EP | 1233083 | | 8/2002 | |
| EP | 1634922 | | 3/2006 | |
| GB | 1405658 | * | 11/1971 | ........... C23C 14/086 |
| WO | 01/61080 | | 8/2001 | |
| WO | WO 01/61080 | A1 * | 8/2001 | ................ C25F 7/00 |
| WO | 2008115883 | | 9/2008 | |

OTHER PUBLICATIONS

Groves (Anodizing of Aluminum, 2006, pp. 1-7, http://nzic.org.nz/ChemProcesses/metals/8E.pdf).*

Pu et al (Angewandte Chemie International Edition, 2001, 40, 8, lines 1490-1493).*

Allam and Grimes (2008) "Effect of cathode material on the morphology and photoelectrochemical properties of vertically oriented TiO2 nanotube arrays" Solar Energy Materials & Solar, Cells 92(11):1468-1475.

Kang et al. (2009) "Fabrication of Highly-Ordered TiO2 Nanotube Arrays and Their Use in Dye-Sensitized Solar Cells" Nano Letters, 9(2):601-606.

Wang et al. (2010) "Fabrication of Highly Ordered TiO2 Nanotube Arrays via Anodization of Ti—6Al—4V Alloy Sheet" Journal of Nanoscience and Nanotechnology, 10(12):8312-8321.

* cited by examiner

DEVICES, SYSTEMS AND METHODS FOR COATING SURFACES

CROSS-REFERENCE TO RELATED APPLICATIONS

Pursuant to 35 U.S.C. § 119(e), this application claims priority to the filing date of U.S. Provisional Application Ser. No. 61/723,773 filed Dec. 3, 2012, the disclosure of which is herein incorporated by reference in its entireties.

INTRODUCTION

Coatings and other surface modifications are utilized to provide beneficial characteristics such as reduced wear and improved biocompatibility to a variety of devices including, for example, implantable medical devices. Metal oxides are versatile materials which are used in a variety of applications including, for example, in optical coatings and as biocompatible coatings for bone implants. Accordingly, new coating techniques and devices, particularly those with applicability to metal oxide coating can be expected to positively affect a variety of important technologies including, for example, medical device fabrication.

SUMMARY

The present disclosure provides devices, systems and methods with applicability in the coating and/or modification of surfaces, in particular three-dimensional surfaces, via anodization reactions. For example, the disclosed devices, systems and methods find use in the formation of microstructured or nanostructured layers, e.g., metal oxide microstructured or nanostructured layers, via anodization on a variety of devices including, e.g., medical devices. Devices modified with one or more microstructured or nanostructured layers are also provided.

Certain non-limiting aspects of the disclosure include a method of forming metal oxide nanotubes on a surface of a structure, the method including positioning a structure including a metal relative to one or more cathodes, wherein the metal is at least 0.1 weight percent of the structure and the structure is in contact with an anode; at least partially submerging the structure and the one or more cathodes in an electrolyte solution; and applying electrical energy between the anode and the one or more cathodes for a period of time sufficient to form at least one metal oxide nanotube on the surface of the structure.

In some embodiments, the one or more cathodes include at least three cathodes, and wherein the at least three cathodes are positioned around the positioned structure. In certain embodiments, the structure comprising the metal is positioned at an equal distance from each of the at least three cathodes. In further embodiments, the step of applying electrical energy between the anode and the one or more cathodes includes applying a substantially constant voltage or a substantially constant current for the period of time. In some embodiments, the nanotube includes an oxide of the metal, such as a metal oxide including an oxide of aluminum, niobium, tantalum, titanium, tungsten, zirconium or mixtures thereof. In certain embodiments, the metal oxide includes an oxide of titanium. In certain embodiments, the metal is at least 10 weight percent of the structure, including at least 20 weight percent of the structure, and at least 50 weight percent of the structure.

In some embodiments, the period of time is sufficient to form at least one nanotube with a length of at least 10 nm on the surface of the structure. In further embodiments, the period of time is sufficient to form at least one nanotube with a length of at least 100 nm on the surface of the structure. In still further embodiments, the period of time is sufficient to form at least one nanotube with a length of at least 1000 nm on the surface of the structure.

In some embodiments, the diameter of the at least one nanotube is at least 1 nm to 1,000 nm, including 10 nm to 200 nm. In further embodiments, the diameter of the at least one nanotube is at least 10 nm. In still further embodiments, the diameter of the at least one nanotube is at least 100 nm. In yet further embodiments, the diameter of the at least on nanotube is a diameter in the range of from 1 nm to 100 nm.

In some embodiments, the step of applying electrical energy between the anode and the one or more cathodes includes applying a substantially constant voltage for the period of time. In certain embodiments, the substantially constant voltage is a substantially constant voltage in the range of from about 1 millivolt to 100 kilovolts, including the range of from about 10 volts to 150 volts.

In some embodiments, the step of applying electrical energy between the anode and the one or more cathodes includes applying a substantially constant current for the period of time. In certain embodiments, the substantially constant current is a substantially constant current in the range of from about 1 femtoampere to about 100 kiloamperes.

In some embodiments, the electrolyte solution includes compounds of aluminum, niobium, tantalum, titanium, tungsten, zirconium or mixtures thereof. In some embodiments, the structure includes a medical device or a portion thereof, including a stent, sensor, arteriovenous shunt, pacemaker, or combinations thereof.

In some embodiments, the method includes maintaining the electrolyte solution at a substantially constant temperature, including a substantially constant temperature above a freezing point of the electrolyte solution and below a boiling point of the electrolyte solution, such as in the range of from about 10° C. to about 50° C. In certain embodiments, the substantially constant temperature is about 25° C. In some embodiments, the period of time is a time in the range of from 5 seconds to 5 days, including a time in the range of from 10 min to 60 min.

In some embodiments, the structure is electropolished prior to the submerging in the electrolyte solution. In some embodiments, the one or more cathodes include aluminum, niobium, tantalum, titanium, tungsten, zirconium or alloys thereof. In other embodiments, the one or more cathodes include graphite.

Other aspects of the disclosure include a coating system including a receiving frame including an anode receiving region, and one or more cathodes positioned around the anode receiving region in the receiving frame; and an anode inserter including an anode, where the receiving frame removably receives the anode inserter and positions the anode in the anode receiving region. In some embodiments, the one or more cathodes include at least three cathodes, and wherein the at least three cathodes are positioned radially around the structure. In other embodiments, the at least three cathodes are positioned at an equal distance to the structure.

In some embodiments, the anode inserter includes a structure including an electrically conductive surface positioned in contact with the anode. In some embodiments, the receiving frame removably receives the anode inserter by slide-fit engagement. In some embodiments, the one or more cathodes include from 4 to 10 cathodes positioned relative to the anode receiving region, including 5 cathodes positioned relative to the anode receiving region.

In some embodiments, the one or more cathodes include platinum, titanium, vanadium, graphite or gold. In some embodiments, the one or more cathodes include platinum wires.

In some embodiments, the anode, when positioned in the anode receiving region, is positioned parallel to the at least three cathodes. In some embodiments, the anode inserter includes a structure including an electrically conductive surface positioned in contact with the anode, and wherein the structure including the electrically conductive surface is positioned parallel to the at least three cathodes. In some embodiments, the structure including the electrically conductive surface includes titanium. In some embodiments, the anode holds the structure including the electrically conductive surface in place and electrically connects the structure including the electrically conductive surface to a power source. In some embodiments, the anode includes graphite, stainless steel or a noble metal, such as platinum.

In some embodiments, the structure including the electrically conductive surface includes a medical device or a portion thereof, such as a stent. In some embodiments, the system further includes a temperature controlled vessel, wherein the receiving frame is positioned in the temperature controlled vessel. In certain embodiments, the temperature controlled vessel includes a jacketed beaker. In certain embodiments, the receiving frame has an external diameter which is less than an internal diameter of the jacketed beaker.

Another aspect of the disclosure includes a coating system that includes a receiving frame including an anode, a receiving region, and one or more cathodes positioned around the anode and the positioned receiving region in the receiving frame; and an inserter including an inserter arm, where the receiving frame removably receives the inserter, positioning the inserter arm in the receiving region.

In some embodiments, the one or more cathodes include at least three cathodes, and where the at least three cathodes are positioned relative to the structure. In certain embodiments, the at least three cathodes are positioned at an equal distance to the structure. In some embodiments, the inserter includes a structure including an electrically conductive surface, which structure is held by the inserter arm.

Yet another aspect of the disclosure includes coating device coating including a first plate defining an anode receiving opening and at least three cathode receiving openings positioned relative the anode receiving opening; a second plate positioned in opposition to the first plate and including at least three cathode receiving openings; a plurality of supports separating the first and second plates; a receiving region between the first and second plates; at least three cathodes extending through the at least three cathode receiving openings of the first plate and into the at least three cathode receiving openings of the second plate; and an anode extending through the anode receiving opening and contacting a structure including an electrically conductive surface when the structure including the electrically conductive surface is positioned in the receiving region.

In some embodiments, the coating device further includes a structure having an electrically conductive surface positioned in the receiving region in contact with the anode. In some embodiments, the at least three cathodes include from 4 to 10 cathodes positioned relative to the receiving region, including at least 5 cathodes. In some embodiments, the at least three cathodes include platinum, titanium, vanadium, graphite or gold. In some embodiments, the at least three cathodes include platinum wires. In some embodiments, the anode is positioned parallel to the at least three cathodes.

In some embodiments, the coating device includes a structure including an electrically conductive surface positioned in contact with the anode, and wherein the structure including the electrically conductive surface is positioned parallel to the at least three cathodes. In certain embodiments, the structure including the electrically conductive surface includes titanium.

In some embodiments, the anode holds the structure including the electrically conductive surface in place and electrically connects the structure including the electrically conductive surface to a power source. In certain embodiments, the anode includes stainless steel, graphite or a noble metal, such as platinum. In some embodiments, the structure including the electrically conductive surface is a medical device or a portion thereof, such as a stent.

Yet another aspect of the disclosure includes a coating system including the coating device described above and a temperature controlled vessel, wherein the coating device is positioned in the temperature controlled vessel. In some embodiments, the temperature controlled vessel includes a jacketed beaker. In some embodiments, the coating device has an external diameter which is less than an internal diameter of the jacketed beaker.

Yet another aspect of the disclosure includes a coating system including the coating device described above and an inserter including an inserter arm, where the coating device removably receives the inserter, and positioning the inserter arm in the receiving region. In some embodiments, the inserter includes a structure including an electrically conductive surface, which structure is held by the inserter arm. In some embodiments, the anode inserter includes a base defining a cutout portion and the inserter arm extends from the cutout portion, where the cutout portion releasably engages external surfaces of the coating device via slide-fit engagement and the arm positions the structure including the electrically conductive surface, when present, in the receiving region of the coating device when the inserter and the coating device are engaged.

DEFINITIONS

Figure 1:
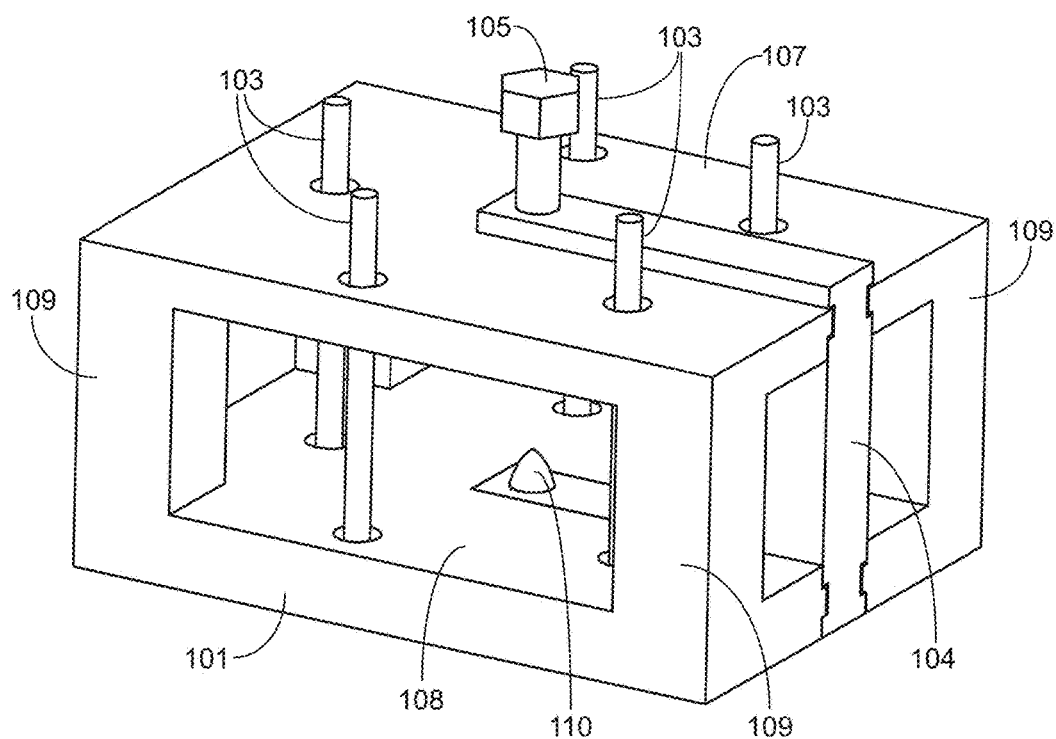
FIG. 1 shows a perspective view of an embodiment of a coating system according to the present disclosure wherein an anode inserter is positioned in a receiving frame. Five cathodes are shown positioned in the receiving frame relative to an anode receiving region.

As used herein, the term "anode" refers to a positively charged electrode of an electrolytic cell or an electrode which is capable of serving as a positively charged electrode of an electrolytic cell.

As used herein, the term "cathode" refers to a negatively charged electrode of an electrolytic cell or an electrode which is capable of serving as a negatively charged electrode of an electrolytic cell.

The term "conductive polymer" means an electrically conductive polymeric material.

As used herein, the terms "nanostructure", "nanostructured" and the like refer to structures or objects modified with structures having at least one dimension greater than 0.1 nm and less than 1000 nm.

As used herein, the terms "microstructure", "microstructured" and the like refer to structures or objects modified with structures having at least one dimension greater than or equal to 1 µm and less than 1000 µm.

As used herein, the terms "determining," "measuring," "assessing," and "assaying" are used interchangeably and include both quantitative and qualitative determinations unless the context clearly indicates otherwise.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an electrode" includes a plurality of such electrodes and reference to "the coating device" includes reference to one or more coating devices and equivalents thereof known to those skilled in the art, and so forth. It is further noted that the claims may be drafted to exclude any element. As such, this statement is intended to serve as antecedent basis for use of such exclusive terminology as "solely," "only" and the like in connection with the recitation of claim elements, or use of a "negative" limitation.

To the extent the disclosure found herein, including the definition or usage of any term herein, conflicts with a disclosure, including a definition or usage of a term, in an application or reference incorporated by reference herein, the instant application shall control.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

As noted above, the present disclosure provides devices, systems and methods with applicability in the coating and/or modification of surfaces, in particular three-dimensional surfaces, via anodization reactions. For example, the disclosed devices, systems and methods find use in the formation of microstructured or nanostructured layers, e.g., metal oxide microstructured or nanostructured layers, via anodization on a variety of devices including, e.g., medical devices. Devices modified with one or more microstructured or nanostructured layers are also provided. In some embodiments, the disclosed devices, systems and methods find use in the formation of microstructured layers including, e.g., microfibers, microtubes, microchannels or microwells. In some embodiments, the disclosed devices, systems and methods find use in the formation of nanostructured layers including, e.g., nanofibers, nanotubes, nanochannels or nanowells. Additional description of the above structures can be found, for example, in U.S. Patent Application Publication Nos. 2010/0318193 and 2012/0114734, the disclosures of each of which are incorporated by reference herein in their entireties.

In some embodiments, the disclosed devices, systems and methods find use in the formation of metal oxide, e.g., titanium dioxide ($TiO_2$) microstructured or nanostructured layers including metal oxide, e.g., $TiO_2$, microfibers, microtubes, microchannels, microwells, nanofibers, nanotubes, nanochannels or nanowells. Devices modified with one or more metal oxide, e.g., $TiO_2$, microstructured or nanostructured layers are also provided.

Coating Devices and Systems

With reference to FIGS. 1-4, the present disclosure provides a coating system 100 including a receiving frame 101. Receiving frame 101 includes an anode receiving region 102 and one or more cathodes 103, e.g., at least three cathodes 103, positioned around, e.g., equidistantly, the anode receiving region 102 in the receiving frame 101. The coating system 100 also includes an anode inserter 104 including an anode 105. The receiving frame 101 removably receives the anode inserter 104 and positions the anode 105 in the anode receiving region 102. The anode inserter 104 can be used to insert a structure including an electrically conductive surface, e.g., a structure including a metal surface, e.g., a medical device such as a stent, (not shown) which is positioned in contact with the anode 105 and inserted into the anode receiving region 102 prior to coating and/or surface modification of the structure or a portion thereof via anodization. Accordingly, in some embodiments, the anode inserter 104 includes a structure including an electrically conductive surface, e.g., a metal surface, (not shown) positioned in contact with the anode 105.

The receiving frame 101 and the anode inserter 104 may be made of any suitable non-conductive material, including, for example, any suitable non-conductive polymer, co-polymer, or polymer combination. Suitable non-conductive polymers may include thermoplastic polymers, e.g., acrylonitrile butadiene styrene (ABS), polyethylene (PE), polypropylene (PP), polystyrene (PS), polyvinyl chloride (PVC), and polyetheretherketone (PEEK), fluorinated polymers, e.g., polytetrafluoroethylene (PTFE) (Teflon™), among others. Generally, the non-conductive material should be selected such that it is compatible and non-reactive under the selected anodization conditions, e.g., with the selected electrolyte solution.

The receiving frame 101 and the anode inserter 104 may be made by a variety of suitable processes, including for example, 3D printing, molding (e.g., injection molding), extrusion and the like. In addition, one or more of the above processes may be utilized to form the receiving frame 101 and/or the anode inserter 104 as a whole or as component parts which may then be assembled to form the receiving frame 101 and/or the anode inserter 104.

The receiving frame 101 is depicted in FIGS. 1-4 as having a generally cuboid shape with open sides, including a first (top) plate 107, a second (bottom) plate 108, and supports 109. However, it should be noted that the present disclosure is not limited to this specific embodiment, and the receiving frame 101 may be provided in a variety of suitable shapes. For example, the top and bottom plates (107 and 108) of receiving frame 101 may have a generally circular shape or any other suitable shape provided that the general configuration of the cathodes 103 with respect to the anode receiving region 102 is maintained. For example, in some embodiments the receiving frame 101 has an external diameter which is less than the internal diameter of a temperature controlled vessel, e.g., a jacketed beaker (not shown), to facilitate positioning of the receiving frame 101 in the temperature controlled vessel, e.g., jacketed beaker, during anodization. A jacketed beaker may be useful, for example, where it is desirable to control the temperature of an electrolyte solution in which anodization is taking place. In some embodiments, a coating system 100 may include an optional temperature sensor (not shown) which may be used independently or in connection with a jacketed beaker to control the temperature of an electrolyte solution during anodization. In some embodiments, the receiving frame 101 may be modified to include an optional temperature sensor or provide a location for positioning of an optional temperature sensor. For example, one or more of first plate 107, second plate 108 and supports 109 may be modified to define an opening configured to receive a temperature sensor.

In addition the number, position and shape of the supports 109 may vary. For example, the receiving frame 101 may include any suitable number or shape of supports 109 provided that the supports 109 are able to maintain sufficient rigidity of the receiving frame 101 to maintain the relative positions of the top and bottom plates (107 and 108). For example, in some embodiments, the receiving frame 101 includes 1, 2, 3, 4, 5, 6, 7, 8, 9, 10 or more supports 109.

The cathodes 103 may be made from or coated with a variety of suitable materials known in the art, e.g., platinum, titanium, vanadium, gold, aluminum, copper, lead, nickel, palladium, iron, cobalt, tantalum, tungsten, graphite, tin, and alloys including one or more of the above. See, e.g., Allam and Grimes, *Solar Energy Materials & Solar Cells* 92 (2008) 1468-1475, the disclosure of which is incorporated by reference herein. In some embodiments, one or more of the cathodes may serve as a sacrificial cathode which is at least partially consumed during the anodization reaction. In addition, the length and diameter of the cathodes 103 may vary depending on particular application of the system. For example, in some embodiments the cathodes 103 may have a diameter of from about 0.2 mm to about 5 mm or greater, e.g., from about 0.3 mm to about 5 mm, about 0.4 mm to about 5 mm, about 0.5 mm to about 5 mm, about 0.6 mm to about 5 mm, about 0.7 to about 5 mm, about 0.8 mm to about 5 mm, about 0.9 mm to about 5 mm, about 1 mm to about 5 mm, about 2 mm to about 5 mm, about 3 mm to about 5 mm, or about 4 mm to about 5 mm. In some embodiments, the cathodes 103 may have a diameter of from about 5 mm to about 0.2 mm, e.g., from about 4 mm to about 0.2 mm, from about 3 mm to about 0.2 mm, from about 2 mm to about 0.2 mm, from about 1 mm to about 0.2 mm, from about 0.9 mm to about 0.2 mm, from about 0.8 mm to about 0.2 mm, from about 0.7 mm to about 0.2 mm, from about 0.6 mm to about 0.2 mm, from about 0.5 mm to about 0.2 mm, from about 0.4 mm to about 0.2 mm, or from about 0.3 mm to about 0.2 mm. In some embodiments, the cathodes 103 are selected such that the total cathode surface area is at least three times the surface area of the structure to be coated and/or surface-modified, e.g., at least four times. The cathodes 103 may be provided in a variety of forms, e.g., as wires, cylinders, cuboids, or any other suitable form. In addition, as discussed in greater detail below, the cathodes 103 may be in the form of a sheet or mesh which at least partially surrounds the anode 105 and/or the structure to be anodized, e.g., in a 360 deg. configuration relative to the anode 105 and/or the structure to be anodized.

The distance between the cathodes 103 and the anode receiving region 102 and/or the structure including the electrically conductive surface may vary depending on the particular application of the system. For example, in some embodiments the cathodes 103 are positioned in a generally circular arrangement around the anode receiving region 102 and/or the structure including the electrically conductive surface, wherein the generally circular arrangement has a radius of from about 10 mm to about 200 mm, e.g., from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, from about 90 mm to about 100 mm, from about 100 mm to about 110 mm, from about 110 mm to about 120 mm, from about 120 mm to about 130 mm, from about 130 mm to about 140 mm, from about 140 mm to about 150 mm, from about 150 mm to about 160 mm, from about 160 mm to about 170 mm, from about 170 mm to about 180 mm, from about 180 mm to about 190 mm, or from about 190 mm to about 200 mm. It should be noted that the radius of the generally circular arrangement may be increased with an increase in the size, e.g., length and/or diameter, of the structure to be coated and/or surface-modified. For example, for many smaller medical devices, e.g., smaller stents having a length of about 15 mm and a diameter of about 2 mm, a radius of from about 10 mm to about 15 mm may be appropriate. For larger structures, e.g., larger stents, the radius may be increased up to at least 50 mm, e.g., at least 200 mm.

Figure 2:
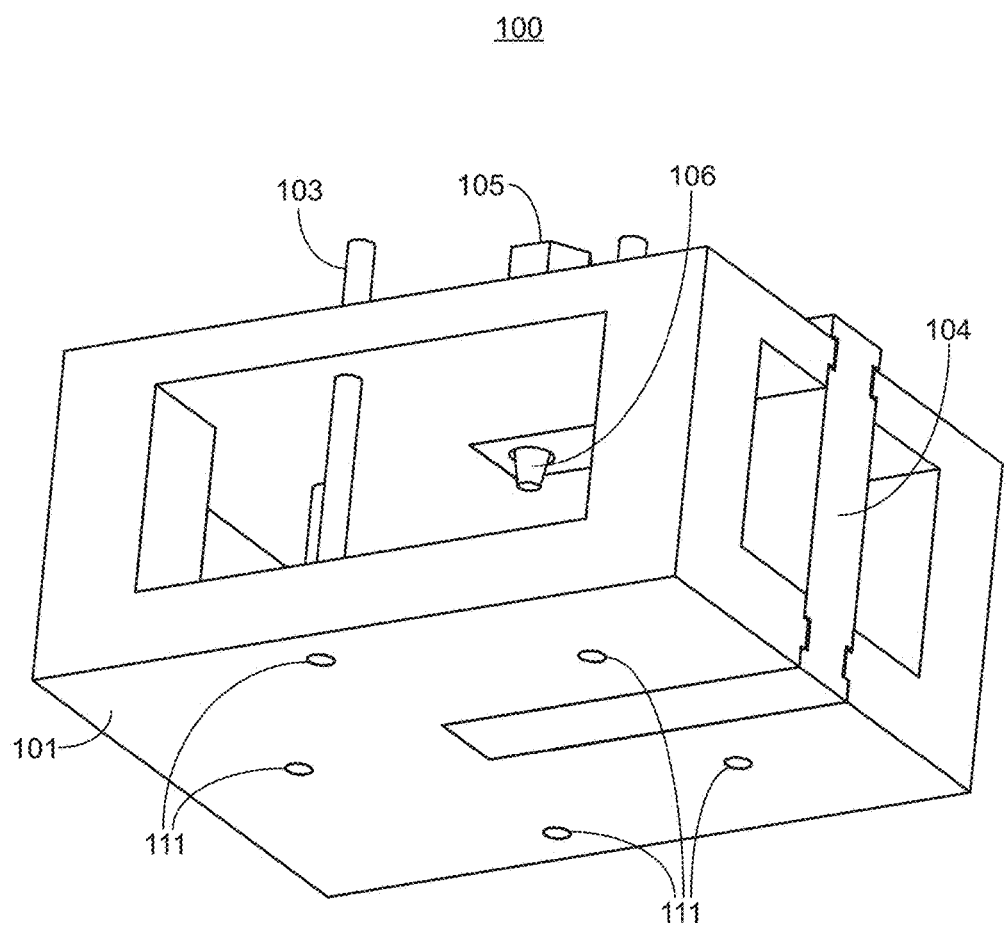
FIG. 2 shows another perspective view of the embodiment shown in FIG. 1.

As indicated above, for coating system 100, at least three cathodes 103 are relative to the anode receiving region 102 in the receiving frame 101. Although five cathodes 103 are shown in FIGS. 1 and 2, it should be noted that the present disclosure is not limited to this specific embodiment, and the number of cathodes 103 may vary, e.g., the number of cathodes 103 may be 1 or more, 2 or more, 3 or more, 4 or more, 5 or more, 10, or more, 50 or more or 100 or more. In some embodiments, the number of cathodes 103 is from 3 to 100, e.g., from 4 to 100, from 5 to 100, from 10 to 100, or from 50 to 100.

It should be noted that while some embodiments herein are described as including at least three cathodes 103 positioned circumferentially around the anode receiving region 102, other suitable cathode arrangements are possible and considered within the scope of the present disclosure, provided that they facilitate the anodization of a three dimensional surface, e.g., the surface defined by the perimeter and height of a generally cylindrical structure. For example, in some embodiments, receiving frame 101 and anode inserter 104 may be configured such that, when engaged, the anode 105 and/or the structure to be anodized are positioned with a single circular cathode or cathode sheet or mesh surrounding the anode 105 and/or the structure to be anodized.

Figure 3:
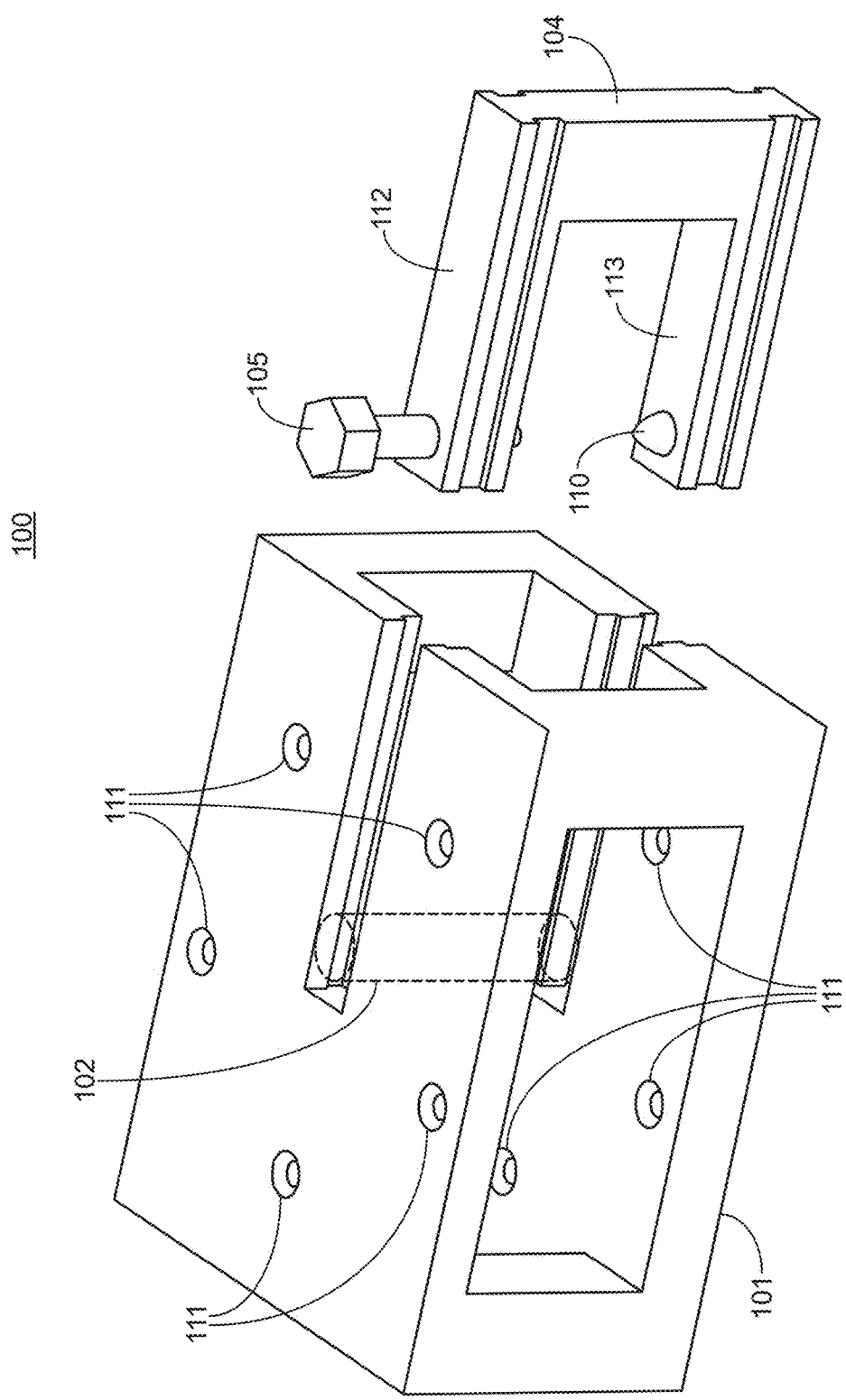
FIG. 3 shows a perspective view of the embodiment shown in FIGS. 1 and 2 with the cathodes removed and the anode inserter removed from the receiving frame.

The cathodes 103 may be inserted or incorporated into the receiving frame 101 in a variety of suitable ways. For example, as shown in FIG. 3, first plate 107 may be structured to define cathode receiving openings 111. Similarly, second plate 108 may be structured to define cathode receiving openings 111. Cathodes 103 may be inserted into and/or through the cathode receiving openings 111 positioned in the first and second plates, e.g., as shown in FIGS. 1 and 2. Alternatively, receiving frame 101 could be formed, e.g., molded, around cathodes 103 without providing cathode receiving openings 111.

The anode 105 may be made from or coated with a variety of suitable conductive materials known in the art, e.g., metals (including any of the noble metals, e.g., ruthenium, rhodium, palladium, silver, osmium, iridium, platinum, gold, and alloys including one or more of the above), alloys (e.g., stainless steel), conductive polymers and the like. Suitable conductive polymers may include one or more intrinsically conductive polymer (ICP). Examples of suitable ICPs can include polyacetylene, poly(p-phenylene vinylene) (PPV), polythiophene, poly(3-alkylthiophene), poly(3,4-ethylenedioxythiophene) (PEDOT), poly(p-phenylene sulfide) (PPS), polyaniline (PANI), polypyrrole, polycarbazole, polyindole, polyazepine, polynaphthalene, polyazulene, polypyrene, polyphenylene, polyfluorene, and combinations, derivatives, and copolymers thereof.

Figure 4:
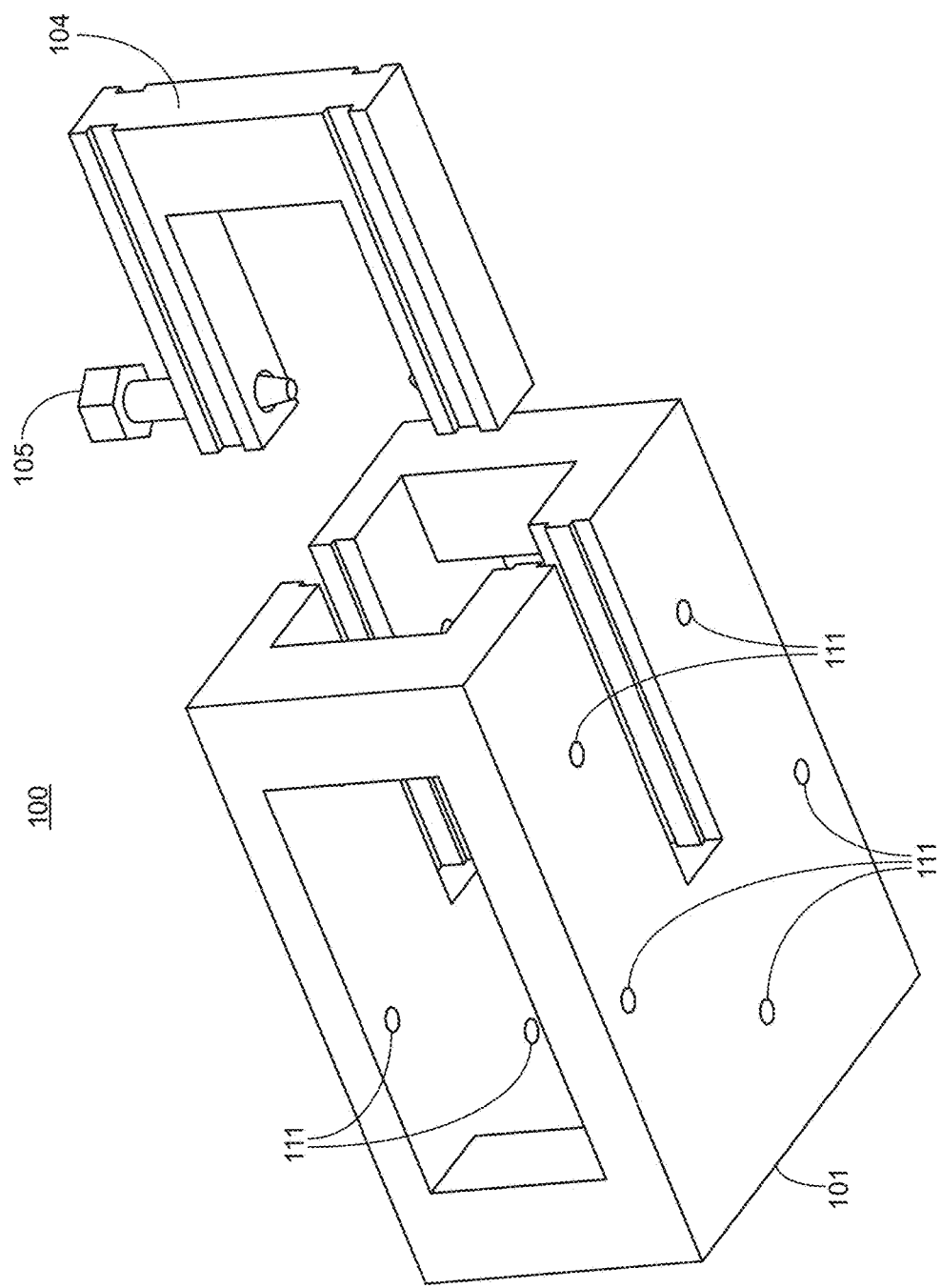
FIG. 4 shows another perspective view of the embodiment shown in FIG. 3.

Although anode 105 is depicted in the form of a screw in FIGS. 1-4, it should be noted that the present disclosure is not limited to this specific embodiment, and the anode 105 may be provided in a variety of forms, provided that it is capable of providing an electrical connection to the structure including an electrically conductive surface which is to be coated and/or surface modified via anodization. For example, the anode 105 may be provided as a wire, cylinder, cuboid, or any other suitable form. In some embodiments, e.g., as shown in FIGS. 2-4, the anode 105 includes a tapered tip 106 which facilitates positioning of the structure including an electrically conductive surface, e.g., a stent, prior to insertion into the receiving frame 101. The anode 105 may include other structural details which facilitate positioning of the structure including an electrically conductive surface. For example, the anode 105 may include one or more recesses or protrusions of various sizes and shapes, e.g., at the end of the anode 105, into which (or onto which) a portion of the structure including the electrically conductive surface may be positioned. In some embodiments a portion of the anode 105 is coated with a non-conductive material, e.g., a non-conductive polymer as described herein, e.g., PEEK.

The anode 105 may be inserted or incorporated into the anode inserter 104 in a variety of suitable ways. For example, the anode 105 may be inserted into an opening or openings defined by the anode inserter 104, e.g., an opening defined by a portion of a first (upper) 112 or second (lower) 113 arm of a "C" shaped anode inserter 104. Alternatively, inserter 104 could be formed, e.g., molded, around anode 105 to position anode 105 in one or both of first (upper) 112 or second (lower) 113 arm of a "C" shaped anode inserter 104 without providing an opening.

The anode inserter 104 may also include structural details which facilitate positioning of the structure including the electrically conductive surface. For example, as depicted in FIGS. 1 and 3, the anode inserter 104 may include one or more optional projections 110 onto which a portion of the structure including the electrically conductive surface may be positioned. The optional projection 110 is shown in FIGS. 1 and 3 as having a generally conical shape. However, any suitable shape may be utilized, e.g., cylindrical or cuboid. Alternatively or in addition, the anode inserter 104 may include one or more recesses (not shown) of various sizes and shapes into which a portion of the structure including the electrically conductive surface may be positioned.

In some embodiments structural details, such as those described above for the anode 105 and the anode inserter 104, may be used together to hold in place or otherwise position the structure including the electrically conductive surface prior to anodization.

As discussed above, the receiving frame 101 removably receives the anode inserter 104 and positions the anode 105 in the anode receiving region 102. In other words, the anode inserter 104 may be removably positioned in the receiving frame 101 to position the anode 105 in the anode receiving region 102. The receiving frame 101 and the anode inserter 104 may releasably engage each other via a variety of suitable mechanisms known in the art to accomplish the removable receipt and/or the removable positioning discussed above. For example, the receiving frame 101 and the anode inserter 104 may releasably engage each other via slide-fit engagement, snap-fit engagement, press-fit engagement and the like.

When the receiving frame 101 and the anode inserter 104 are fully engaged, the anode 105 is positioned in the anode receiving region 102 with the cathodes 103 positioned relative to the anode receiving region 102. In some embodiments, when positioned in the anode receiving region 102, the anode 105 is positioned parallel to the at least three cathodes 103. Similarly, when the structure including an electrically conductive surface is positioned in the anode inserter 104 in contact with the anode 105, the structure including the electrically conductive surface may be positioned parallel to the at least three cathodes 103.

A coating device 200 according to the present disclosure is now described with reference to FIGS. 5-8. The coating device 200 includes a first (top) plate 201 defining an anode receiving opening 202 and at least three cathode receiving openings 203 positioned radially relative to the anode receiving opening 202. A second (bottom) plate 204 is positioned in opposition to the first plate 201 and defines at least three cathode receiving openings 203. Supports 205 separate the first and second plates (201 and 204). The above structure forms a receiving region 206 between the first and second plates (201 and 204). At least three cathodes 207 extend into and/or through the at least three cathode receiving openings 203 of the first plate and into and/or through the at least three cathode receiving openings 203 of the second plate 204. An anode 208 extends through the anode receiving opening 202 and contacts a structure including an electrically conductive surface, e.g., a medical device such as a stent, (not shown) when the structure including the electrically conductive surface is positioned in the positioned receiving region 206 prior to coating and/or surface modification of the structure or a portion thereof via anodization. Accordingly, in some embodiments, the coating device 200 includes a structure including an electrically conductive surface (not shown) positioned in contact with the anode 208. In some embodiments, e.g., as shown in FIGS. 5-8, the coating device 200 includes optional base supports 209 positioned to support second (bottom) plate 204.

The non-conductive components of the coating device 200, e.g., the first (top) plate 201, second (bottom) plate 204, supports 205 and optional base supports 209 may be made of any suitable non-conductive material, including, for example, any suitable non-conductive polymer, co-polymer, or polymer combination. Suitable non-conductive polymers may include thermoplastic polymers, e.g., acrylonitrile butadiene styrene (ABS), polyethylene (PE), polypropylene (PP), polystyrene (PS), polyvinyl chloride (PVC), and polyetheretherketone (PEEK), fluorinated polymers, e.g., polytetrafluoroethylene (PTFE) (Teflon™), among others. Generally, the non-conductive material should be selected such that it is compatible and non-reactive under the selected anodization conditions, e.g., with the selected electrolyte solution.

The first (top) plate 201, second (bottom) plate 204, supports 205 and optional base supports 209 may be made by a variety of suitable processes, including for example, 3D printing, molding (e.g., injection molding), extrusion and the like. In addition, one or more of the above processes may be utilized to form the first (top) plate 201, second (bottom) plate 204, supports 205 and optional base supports 209 together as a whole or as component parts which may then be assembled as a whole.

The coating device 200 is depicted in FIGS. 5-8 as having a generally cylindrical shape with open sides. However, it should be noted that the present disclosure is not limited to this specific embodiment, and the coating device 200 may be provided in a variety of suitable shapes. For example, the top and bottom plates (201 and 204) may have a generally square or rectangular shape or any other suitable shape provided that the general configuration of the cathodes 207 with respect to the receiving region 206 is maintained. In addition the number, position and shape of the supports 205 may vary. For example, the coating device 200 may include any suitable number or shape of supports 205 provided that the supports 205 are able to maintain sufficient rigidity of the coating device 200 to maintain the relative positions of the top and bottom plates (201 and 204). For example, in some embodiments, the coating device 200 includes 1, 2, 3, 4, 5, 6, 7, 8, 9, 10 or more supports 205. Similarly, the number, position and shape of optional base supports 209 may vary.

The cathodes 207 may be made from or coated with a variety of suitable materials known in the art, e.g., platinum, titanium, vanadium, gold, aluminum, copper, lead, nickel, palladium, iron, cobalt, tantalum, tungsten, graphite, tin, and alloys including one or more of the above. See, e.g., Allam and Grimes, *Solar Energy Materials & Solar Cells* 92 (2008) 1468-1475, and Wang et al., Journal of Nanoscience and Nanotechnology, (2010) Vol. 10, No. 12, pp. 8312-8321, the disclosures of each of which are incorporated by reference herein. In addition, the length and diameter of the cathodes 207 may vary depending on particular application of the system. For example, in some embodiments the cathodes 207 may have a diameter of from about 0.2 mm to about 5 mm or greater, e.g., from about 0.3 mm to about 5 mm, about 0.4 mm to about 5 mm, about 0.5 mm to about 5 mm, about 0.6 mm to about 5 mm, about 0.7 to about 5 mm, about 0.8 mm to about 5 mm, about 0.9 mm to about 5 mm, about 1 mm to about 5 mm, about 2 mm to about 5 mm, about 3 mm to about 5 mm, or about 4 mm to about 5 mm. In some embodiments, the cathodes 207 may have a diameter of from about 5 mm to about 0.2 mm, e.g., from about 4 mm to about 0.2 mm, from about 3 mm to about 0.2 mm, from about 2 mm to about 0.2 mm, from about 1 mm to about 0.2 mm, from about 0.9 mm to about 0.2 mm, from about 0.8 mm to about 0.2 mm, from about 0.7 mm to about 0.2 mm, from about 0.6 mm to about 0.2 mm, from about 0.5 mm to about 0.2 mm, from about 0.4 mm to about 0.2 mm, or from about 0.3 mm to about 0.2 mm. In some embodiments, the cathodes 207 are selected such that the total cathode surface area is at least three times the surface area of the structure to be coated and/or surface modified, e.g., at least four times. The cathodes 207 may be provided in a variety of forms, e.g., as wires, cylinders, cuboids, or any other suitable form.

The distance between the cathodes 207 and the receiving region 206 and/or the structure including the electrically conductive surface may vary depending on the particular application of the system as well as the shape and size of the electrically conductive surface positioned in the receiving region 206. For example, in some embodiments, the cathodes are all placed at substantially an equal distance from the electrically conductive surface. The positioning of the cathodes in relation to the electrically conductive surface will generally follow the cross-sectional shape of the electrically conductive surface. For example, in embodiments in which the electrically conductive surface has a generally rectangular, square or non-circular cross-section, then the cathodes 207 are placed in a pattern corresponding to the cross-sectional shape around the electrically conductive surface. In such embodiments, the cathodes are all placed at substantially an equal distance from the electrically conductive surface of from about 10 mm to about 300 mm or more, e.g., from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, from about 90 mm to about 100 mm, from about 100 mm to about 110 mm, from about 110 mm to about 120 mm, from about 120 mm to about 130 mm, from about 130 mm to about 140 mm, from about 140 mm to about 150 mm, from about 150 mm to about 160 mm, from about 160 mm to about 170 mm, from about 170 mm to about 180 mm, from about 180 mm to about 190 mm, from about 190 mm to about 200 mm, from about 200 mm to about 250 mm, or from about 250 mm to about 300 mm or more.

Moreover, in embodiments in which the electrically conductive surface has a generally circular cross-section and having the shape of a generally tubular or cylindrical form (including, for example, a stent), the cathodes 207 are positioned in a generally circular arrangement (e.g., radially or circumferentially) around the centrally positioned receiving region 206 and/or the structure including the electrically conductive surface, wherein the generally circular arrangement has a radius of from about 10 mm to about 300 mm or more, e.g., from about 10 mm to about 20 mm, from about 20 mm to about 30 mm, from about 30 mm to about 40 mm, from about 40 mm to about 50 mm, from about 50 mm to about 60 mm, from about 60 mm to about 70 mm, from about 70 mm to about 80 mm, from about 80 mm to about 90 mm, from about 90 mm to about 100 mm, from about 100 mm to about 110 mm, from about 110 mm to about 120 mm, from about 120 mm to about 130 mm, from about 130 mm to about 140 mm, from about 140 mm to about 150 mm, from about 150 mm to about 160 mm, from about 160 mm to about 170 mm, from about 170 mm to about 180 mm, from about 180 mm to about 190 mm, from about 190 mm to about 200 mm, from about 200 mm to about 250 mm, or from about 250 mm to about 300 mm or more. It should be noted that the radius of the generally circular arrangement may be increased with an increase in the size, e.g., length and/or diameter, of the structure to be coated and/or surface-modified. For example, for many smaller medical devices, e.g., smaller stents having a length of about 15 mm and a diameter of about 2 mm, a radius of from about 10 mm to about 15 mm may be appropriate. For larger structures, e.g., larger stents, the radius may be increased up to at least 50 mm, e.g., at least 200 mm.

Figure 5:
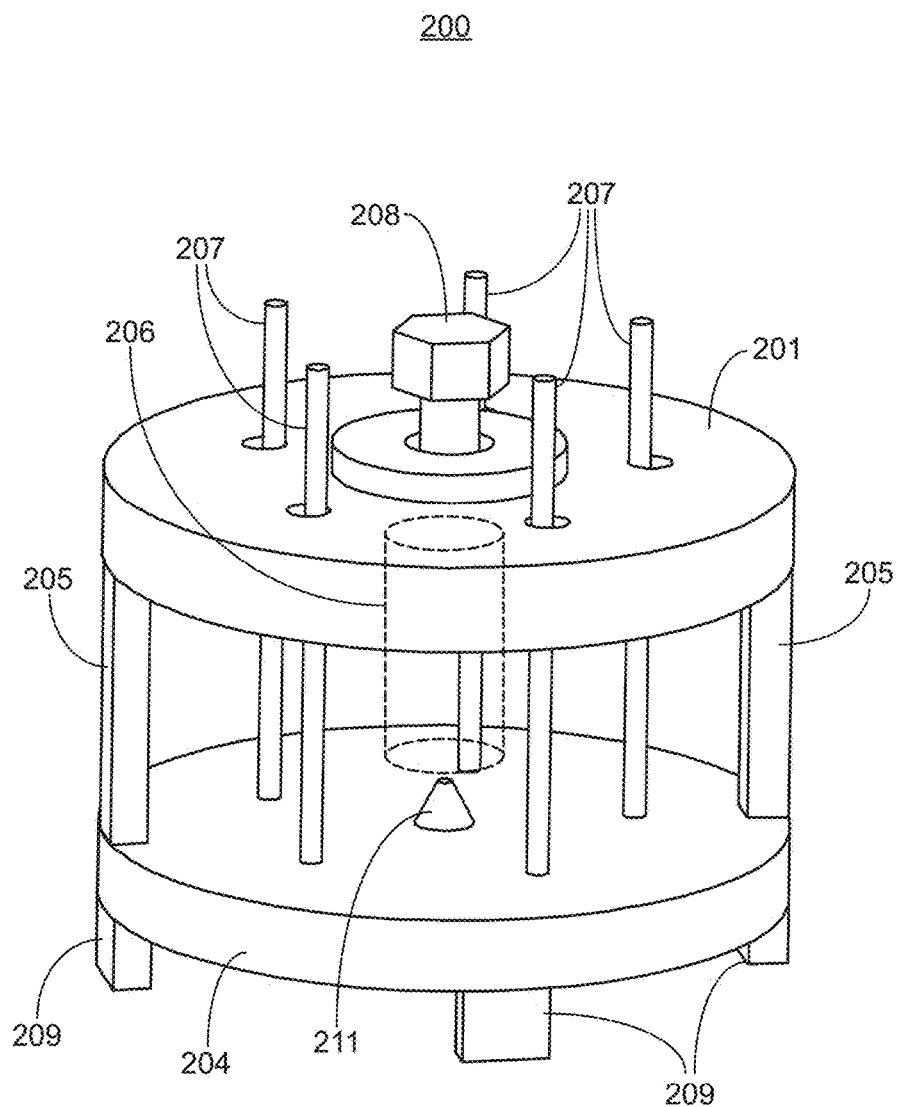
FIG. 5 shows a perspective view of an embodiment of a coating device according to the present disclosure wherein five cathodes are positioned relative to an anode and a receiving region.
Figure 6:
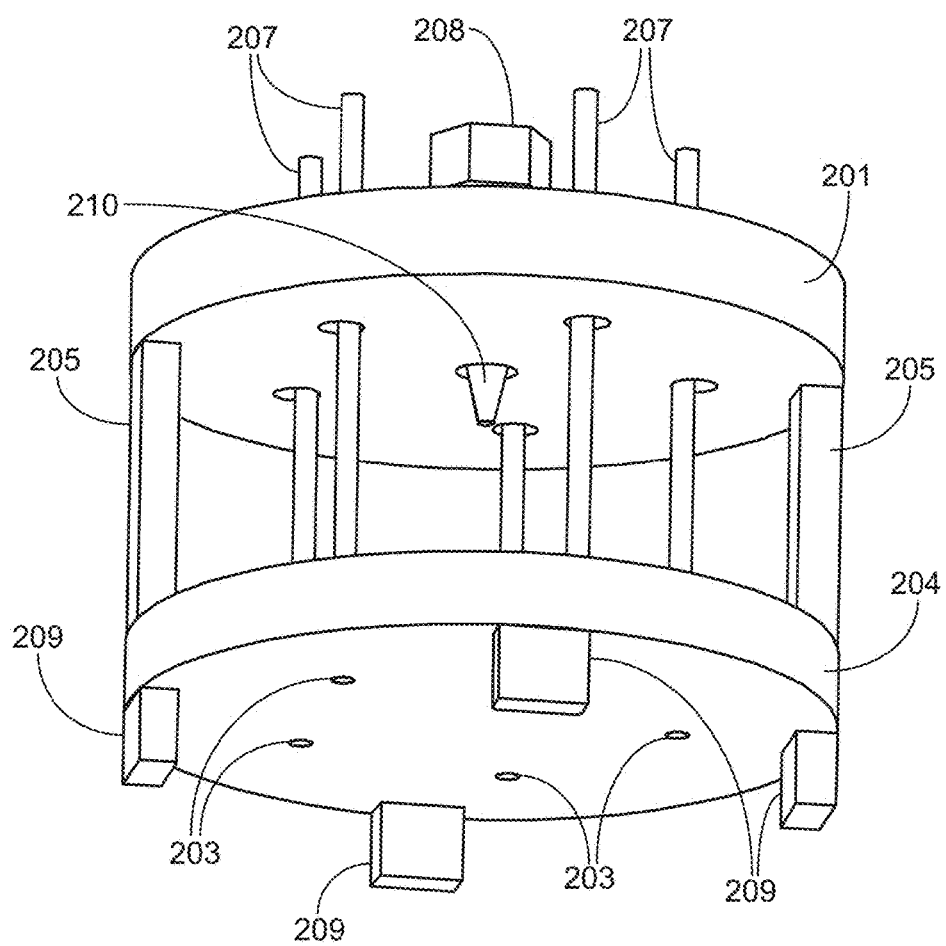
FIG. 6 shows another perspective view of the embodiment of FIG. 5.

As indicated above, for coating device 200, at least three cathodes 207 are positioned relative to the receiving region 206 in the coating device 200. Although five cathodes 207 are shown in FIGS. 5 and 6, it should be noted that the present disclosure is not limited to this specific embodiment, and the number of cathodes 207 may vary, e.g., the number of cathodes 207 may be 1 or more, 2 or more, 3 or more, 4 or more, 5 or more, 10, or more, 50 or more or 100 or more. In some embodiments, the number of cathodes 207 is from 3 to 100, e.g., from 4 to 100, from 5 to 100, from 10 to 100, or from 50 to 100.

It should be noted that while some embodiments herein are described as including at least three cathodes 207 positioned radially around the centrally positioned receiving region 206, other suitable cathode arrangements are possible and considered within the scope of the present disclosure, provided that they facilitate the anodization of a three dimensional surface, e.g., the surface defined by the perimeter and height of a generally cylindrical structure. For example, in some embodiments, the coating device 200 and the anode 208 and/or the structure to be anodized are positioned with a single circular cathode or cathode sheet or mesh surrounding the anode 208 and/or the structure to be anodized.

Figure 7:
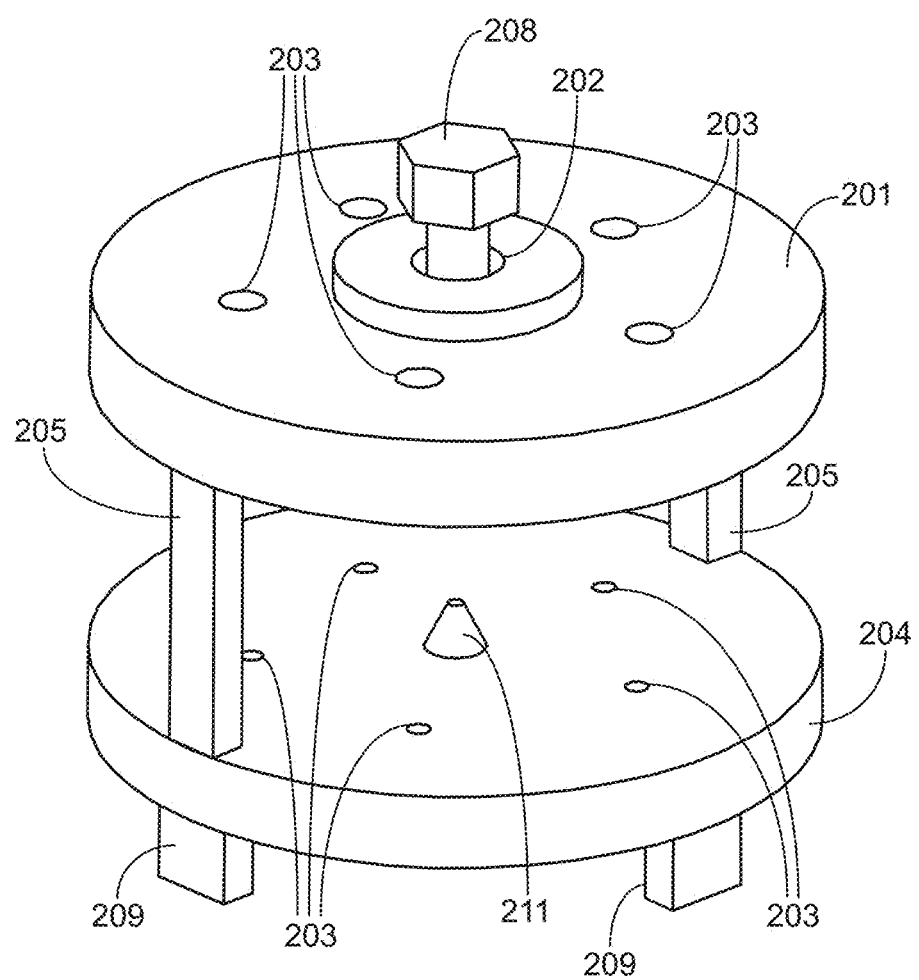
FIG. 7 shows a perspective view of the embodiment shown in FIGS. 5 and 6 with the cathodes removed.

The cathodes 207 may be inserted or incorporated into the coating device 200 in a variety of suitable ways. For example, as shown in FIG. 7 first plate 201 may be structured to define cathode receiving openings 203. Similarly, second plate 204 may be structured to define cathode receiving openings 203. Cathodes 207 may be inserted into and/or through the cathode receiving openings 203 positioned in the first and second plates, e.g., as shown in FIGS. 5 and 6. Alternatively, coating device 200 could be formed, e.g., molded, around cathodes 207 without providing cathode receiving openings 203.

The anode 208 may be made from or coated with a variety of suitable conductive materials known in the art, e.g., metals (including any of the noble metals, e.g., ruthenium, rhodium, palladium, silver, osmium, iridium, platinum, gold, graphite and alloys including one or more of the above), alloys (e.g., stainless steel), conductive polymers and the like. Suitable conductive polymers may include one or more intrinsically conductive polymer (ICP). Examples of suitable ICPs can include polyacetylene, poly(p-phenylene vinylene) (PPV), polythiophene, poly(3-alkylthiophene), poly(3,4-ethylenedioxythiophene) (PEDOT), poly (p-phenylene sulfide) (PPS), polyaniline (PANI), polypyrrole, polycarbazole, polyindole, polyazepine, polynaphthalene, polyazulene, polypyrene, polyphenylene, polyfluorene, and combinations, derivatives, and copolymers thereof.

Figure 8:
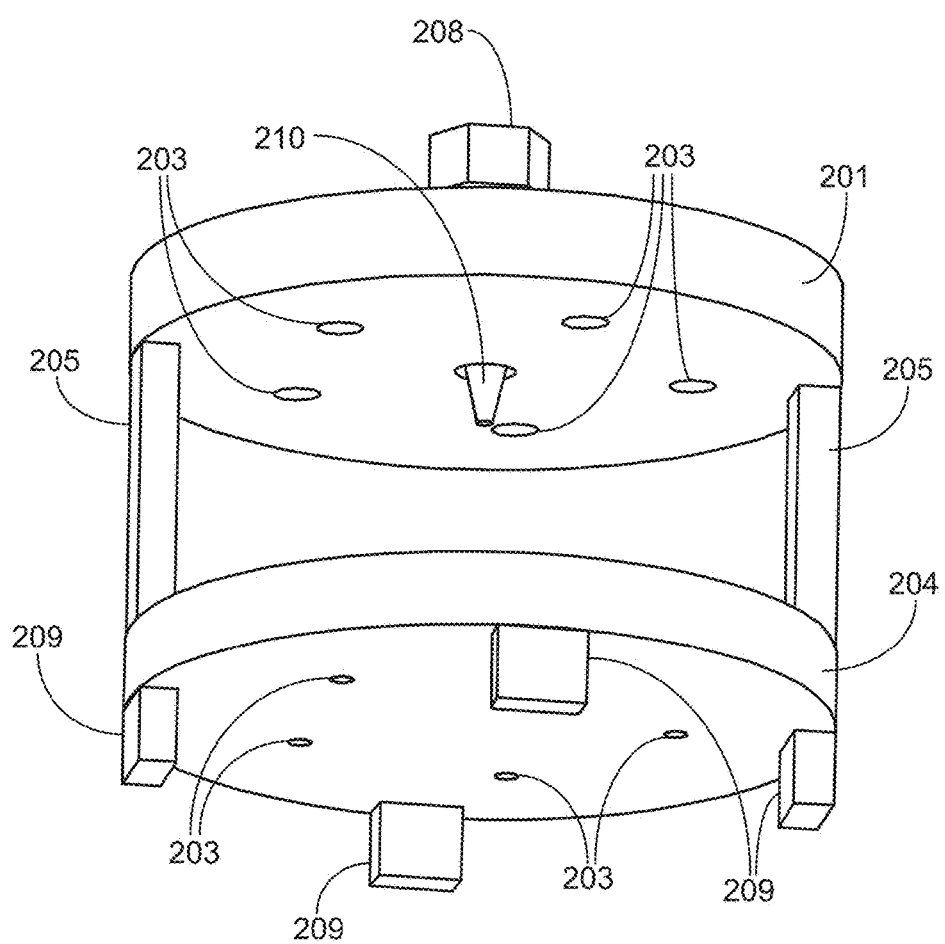
FIG. 8 shows another perspective view of the embodiment shown in FIG. 7.

Although anode 208 is depicted in the form of a screw in FIGS. 5-8, it should be noted that the present disclosure is not limited to this specific embodiment, and the anode 208 may be provided in a variety of forms, provided that it is capable of providing an electrical connection to the structure including an electrically conductive surface which is to be coated and/or surface-modified via anodization. For example, the anode 208 may be provided as a wire, cylinder, cuboid, or any other suitable form. In some embodiments, e.g., as shown in FIGS. 6 and 8, the anode 208 includes a tapered tip 210 which facilitates positioning of the structure including an electrically conductive surface, e.g., a stent, prior to insertion into the coating device 200. The anode 208 may include other structural details which facilitate positioning of the structure including an electrically conductive surface. For example, the anode 208 may include one or more recesses or protrusions of various sizes and shapes, e.g., at the end of the anode 208, into which (or onto which) a portion of the structure including the electrically conductive surface may be positioned. In some embodiments a portion of the anode 208 is coated with a non-conductive material, e.g., a non-conductive polymer as described herein, e.g., PEEK.

The anode 208 may be inserted or incorporated into the coating device 200 in a variety of suitable ways. For example, the anode 208 may be inserted into a anode receiving opening 202 of first plate 201. Alternatively, first plate 201 and/or second plate 204 could be formed, e.g., molded, around anode 208 to position anode 208 in first plate 201 and/or second plate 204 without providing an opening.

In certain embodiments, the receiving opening is positioned such that upon inserting the anode 208 within it results in the anode 208 being positioned in the center of the coating device 208 in relation to the other elements of the coating device. For example, The first plate 201 and/or the second plate 204 may also include structural details which facilitate positioning of the structure including the electrically conductive surface. For example, as depicted in FIGS. 5 and 7, the second plate 204 may include one or more optional projections 211 onto which a portion of the structure including the electrically conductive surface may be positioned. The optional projection 211 is shown in FIGS. 5 and 7 as having a generally conical shape. However, any suitable shape may be utilized, e.g., cylindrical or cuboid. Alternatively or in addition, first plate 201 and/or the second plate 204 may include one or more recesses (not shown) of various sizes and shapes into which a portion of the structure including the electrically conductive surface may be positioned.

In some embodiments structural details, such as those described above for the anode 208 and first plate 201 and/or second plate 204, may be used together to hold in place or otherwise position the structure including the electrically conductive surface prior to anodization.

In some embodiments, a coating device 200 as described above may be used as part of a coating system including additional elements which may be used in the anodization process, e.g., a jacketed beaker. In some embodiments, coating device 200 is specifically configured for use as part of a coating system including a jacketed beaker. For example, in some embodiments, coating device 200 is configured to have an external diameter which is less than an internal diameter of the jacketed beaker. A jacketed beaker may be useful, for example, where it is desirable to control the temperature of an electrolyte solution in which anodization is taking place. In some embodiments, a coating system including a coating device 200 may include an optional temperature sensor (not shown) which may be used independently or in connection with a jacketed beaker to control the temperature of an electrolyte solution during anodization. In such embodiments, the coating device 200 may be modified to include an optional temperature sensor or provide a location for positioning of an optional temperature sensor. For example, one or more of first plate 201, second plate 204 and supports 205 may be modified to define an opening configured to receive a temperature sensor.

In some embodiments, a coating device 200 as described above may be used as part of a coating system including an inserter configured to insert a structure including an electrically conductive surface to be coated and/or surface modified. An exemplary inserter for use with coating device 200 is now described with reference to FIGS. 9 and 10. An inserter 300 includes a base 301 defining a cutout portion 302 and an inserter arm 303 which extends from the cutout portion 302. The cutout portion 302 is configured for slide-fit engagement with external surfaces of the coating device 200 as shown generally in FIGS. 9 and 10. The inserter arm 303 positions the structure including the electrically conductive surface, when present, in the receiving region 206 of the coating device 200 when the inserter 300 and the coating device 200 are engaged. In some embodiments, the inserter arm 303 includes a groove 304 at the distal end of inserter arm 303 which is configured to hold in place or otherwise position a structure including a conductive surface to be coated and/or surface-modified.

Coating Methods

As discussed previously herein, the present disclosure provides methods of coating and/or modifying surfaces, in particular three-dimensional surfaces such as curved surfaces, via anodization reactions. Generally, these methods include positioning a structure including a metal relative to one or more cathodes, wherein the metal is at least 0.1 weight percent of the structure and the structure is in contact with an anode; at least partially submerging the structure and the one or more cathodes in an electrolyte solution; and applying electrical energy between the anode and the one or more cathodes for a period of time sufficient to form at least one metal oxide nanostructures or microstructures, e.g., microfibers, microtubes, microchannels, microwells, nanofibers, nanotubes, nanochannels or nanowells, on a surface of the structure. For example, metal oxide nanostructures or microstructures, e.g., microfibers, microtubes, microchannels, microwells, nanofibers, nanotubes, nanochannels or nanowells are formed, e.g., via anodization, on the structure such that a surface including the microfibers, microtubes, microchannels, microwells, nanofibers, nanotubes, nanochannels or nanowells is provided.

In some embodiments, the disclosed methods are practiced using one or more of the devices and systems described herein. Accordingly, in some embodiments, additional configurations and numbers of cathodes and anodes are possible as described previously. For example, in some embodiments the anode and/or the structure to be anodized are positioned with a single circular cathode or cathode mesh surrounding the anode and/or the structure to be anodized.

In some embodiments, the disclosed methods may be practiced using one or more electro-polishing systems adapted for use with the disclosed methods. Electro-polishing systems are described for example in U.S. Pat. Nos. 6,375,826 and 6,679,980, and U.S. Patent Application Publication Nos. 2007/0209947 and 2007/0209929, the disclosures of each of which are incorporated by reference herein in their entireties. For example, in some embodiments the disclosed methods may utilize an anodization system including, e.g., spinning cathodes or anodes, rotating anodes or cathodes around an axis, etc.

As discussed above, the disclosed methods may include positioning a structure including a metal relative to one or more cathodes. In some embodiments, the structure including a metal may be positioned centrally relative to one or more cathodes. In other embodiments, the structure including a metal may be positioned non-centrally relative to one or more cathodes. For example, in certain embodiments the structure may be positioned closer to one or more cathodes as compared to one or more other cathodes in the electrolytic cell.

In some embodiments, the structure is generally centered with respect to the cathodes, but the cathode arrangement is asymmetric with respect to the structure. For example, asymmetric cathode positioning could include, X number of cathodes positioned generally on a first side of the structure and Y number of cathodes positioned generally on a second side of the structure, where X and Y are integers between 1 and 100 and wherein X and Y are not the same, e.g., two cathodes positioned generally on a first side of the structure and five cathodes positioned generally on a second side of the structure. Other asymmetric cathode arrangements are possible and considered within the scope of the present disclosure.

In some embodiments, the structure is not centered with respect to the one or more cathodes. In such embodiments, the cathodes may be arranged, e.g., symmetrically or asymmetrically, relative to the structure. Cathodes positioned asymmetrically relative to a centrally positioned structure and/or cathodes positioned symmetrically or asymmetrically relative to a non-centrally positioned structure may be useful, for example, where a diameter or length gradient in the nanotubes formed on the surface of the structure is desired.

In some embodiments of the general method described above, following the application of electrical energy between the anode and the one or more cathodes for a period of time, one or more layers of metal oxide nanostructures or microstructures, wherein the metal oxide is an oxide of one of aluminum, niobium, tantalum, titanium, tungsten, and zirconium, are formed on a structure including an electrically conductive surface, e.g., a structure including a metal. For example, in some embodiments a surface including one or more layers of metal oxide nanostructures or microstructures, wherein the metal oxide is an oxide of one of aluminum, niobium, tantalum, titanium, tungsten, and zirconium, is provided.

In some embodiments following the application of electrical energy between the anode and the one or more cathodes, e.g., application of a constant voltage or a constant current for a predetermined period of time, one or more layers of metal oxide nanotubes or nanowells, e.g., $TiO_2$ nanotubes or nanowells, are formed on a structure including an electrically conductive surface. In some embodiments, such metal oxide nanotubes or nanowells have an average length of from about 200 nm to about 600 μm, e.g., from about 200 nm to about 400 mm, from about 400 nm to about 600 nm, from about 600 nm to about 800 nm, from about 800 nm to about 1000 nm, from about 1 μm to about 50 μm, from about 50 μm to about 100 μm, from about 100 μm to about 200 μm, from about 200 μm to about 300 μm, from about 300 μm to about 400 μm, from about 400 μm to about 500 μm, or from about 500 μm to about 600 μm. In some embodiments, such metal oxide nanotubes or nanowells have an average length of from about 400 nm to about 600 μm, from about 600 nm to about 600 μm, from about 800 nm to about 600 μm, from about 1 μm to about 600 μm, from about 50 μm to about 600 μm, from about 100 μm to about 600 μm, from about 200 μm to about 600 μm, or from about 400 μm to about 600 μm.

In some embodiments, such metal oxide nanotubes or nanowells have an average length of from about 0.5 μm to about 10 μm, e.g., from about 1 μm to about 9.5 μm, from about 1.5 μm to about 9 μm, from about 2 μm to about 8.5 μm, from about 2.5 μm to about 8 μm, from about 3 μm to about 7.5 μm, from about 3.5 μm to about 7 μm, from about 4 μm to about 6.5 μm, from about 4.5 μm to about 6 μm, or from about 5 μm to about 5.5 μm.

In some embodiments, metal oxide nanotubes or nanowells produced according to the disclosed methods have an average diameter of from about 1 nm to about 1,000 nm, e.g., from about 10 nm to about 900 nm, from about 50 nm to about 800 nm, from about 100 nm to about 700 nm, from about 200 nm to about 600 nm, from about 300 nm to about 500 nm, or from about 450 nm to about 500 nm. In some embodiments, metal oxide nanotubes or nanowells produced according to the disclosed methods have an average diameter of from about 10 nm to about 200 nm, from about 30 nm to about 180 nm, from about 50 nm to about 160 nm, from about 80 nm to about 140 nm, or from about 100 nm to about 120 nm. In some embodiments, metal oxide nanotubes or nanowells produced according to the disclosed methods have an average diameter of from about 50 nm to about 250 nm, from about 100 nm to about 200 nm, or about 150 nm.

Metal oxide microtubes, microwells, nanotubes or nanowells provided according to the disclosed methods and/or using the disclosed devices and/or systems generally include a lumen or bore defined by one or more side walls. In some embodiments, the microtubes, microwells, nanotubes or nanowells may have a generally tubular structure, a generally conical structure, or a generally frustoconical structure. In some embodiments, a drug (e.g., a bioactive compound) or biologically active agent may be positioned in the lumen or bore of the microtubes, microwells, nanotubes or nanowells described herein. In some embodiments, a material, e.g., a polymeric material (e.g., an erodible polymer) may be positioned over the drug or active agent in the lumen or bore, e.g., to provide for controlled or delayed release of the drug or active agent in vivo. In other words, the drug or active agent containing lumen or bore of the microtubes, microwells, nanotubes or nanowells may be capped with a material, e.g., a polymeric material (e.g., an erodible polymer), e.g., provide for controlled or delayed release of the drug or active agent in vivo. Suitable drug or active agent materials are described, for example, in U.S. Patent Application Publication Nos. 2010/0318193 and 2012/0114734, the disclosures of each of which are incorporated by reference herein in their entireties. It should be noted that materials other than drugs or biologically active agents may be incorporated into the lumen or bore of the microtubes, microwells, nanotubes or nanowells, e.g., where the application of the coated and/or surface-modified structure is for use in a context other than the medical device context. Such materials may include, e.g, compounds, macromolecules, polymers, and the like.

As discussed above, the disclosed methods may include applying a constant voltage or a constant current for a predetermined period of time between the anode and the cathodes or cathode. Where the method includes applying a constant voltage for a predetermined period of time, the constant voltage may be from about 1 mV to about 100 kV, e.g., from about 10 mV to about 10 kV, from about 100 mV to about 1 kV, from about 1 V to about 100 V, or about 10 V. In some embodiments, where the method includes applying a constant voltage for a predetermined period of time, the constant voltage may be from about 10 mV to about 100 kV, from about 100 mV to about 100 kV, from about 1 V to about 100 kV, from about 10 V to about 100 kV, from about 100 V to about 100 kV, from about 1 kV to about 100 kV, or from about 10 kV to about 100 kV. The predetermined period of time may be from about 5 s to about 5 days, e.g., about 10 s to about 5 days, about 30 s to about 5 days, about 1 min to about 5 days, about 5 min to about 5 days, about 10 min to about 5 days, about 30 min to about 5 days, about 1 hour to about 5 days, from about 5 hours to about 5 days, from about 10 hours to about 5 days, or from about 1 day to about 5 days. In some embodiments the predetermined period of time may be from about 5 min to about 90 min, e.g, from about 10 min to about 60 min, from about 20 min to about 50 min, or from about 30 min to about 40 min.

In some embodiments, the disclosed methods include applying a substantially constant voltage in a range of from about 10 V to about 110 V for a period of time within a range of about 5 to 90 min.

Where the method includes applying a constant current for a predetermined period of time, the constant current may be from about 1 fA to about 100 kA, e.g., from about 1 pA to about 100 kA, from about 1 nA to about 100 kA, from about 1 μA to about 100 kA, from about 1 mA to about 100 kA, from about 1 A to about 100 kA, or from about 1 kA to about 100 kA.

In some embodiments, the voltage and/or current may vary during the anodization process. For example, in some embodiments, the voltage may vary between about 1 mV and about 100 kV (or within one of the ranges discussed above) during the anodization process and/or the current may vary between about 1 fA and about 100 kA (or within one of the ranges discussed above).

As indicated above, the disclosed methods generally include at least partially submerging the structure to be coated and/or surface-modified and the cathode or cathodes in an electrolyte solution. A variety of electrolyte solutions may be utilized depending on the particular application of the method, e.g., the desired nanotube dimensions or morphologies, and the materials used, e.g., the composition of the anode and/or the structure to be coated and/or surface-modified and the cathode or cathodes. Suitable electrolytes may include, for example, one or more of ammonium fluoride, a chloride salt (e.g., ammonium chloride, sodium chloride, and potassium chloride), organic nitrates, perchlorate/chloride-containing electrolytes, fluoride-free electrolytes (e.g., sodium chloride and potassium bromide) and other suitable electrolytes known in the art. In some embodiments, in addition to one or more of the above electrolytes, the electrolyte solution may include, e.g., ethylene glycol and/or water.

In some embodiments, an electrolyte solution for use in connection with the disclosed methods includes ethylene glycol, water and ammonium fluoride at a ratio of (9:1:3 g/L).

In some embodiments, the electrolyte solution acts as an etchant for the structure to be coated and/or surface modified.

In some embodiments, the source material from which the one or more microstructures or nanostructures as described are formed is derived from the electrolyte solution via a sol-gel process. For example, the electrolyte solution may include $Ti(OC_3H_7)$ which is converted to $TiO_2$ nanostructures, e.g., nanotubes, on a structure during anodization. In such embodiments, the structure on which the nanostructures, e.g., nanotubes are to be formed, can include, e.g., stainless steel or CoCr. See, e.g., Kang et al. *Nano Letters* (2009), vol. 9, no. 2, pp. 601-606, the disclosure of which is incorporated by reference herein in its entirety.

As discussed previously herein, in some embodiments of the disclosed methods it may be desirable to control the temperature of the electrolyte solution during anodization. For example, a method according to the present disclosure may include maintaining the electrolyte solution at a substantially constant temperature for a period of time. In some embodiments, the substantially constant temperature is above the freezing point of the electrolyte solution and below the boiling point of the electrolyte solution. For example, in some embodiments, the substantially constant temperature may be about 25° C. In some embodiments, the substantially constant temperature may exceed the boiling point of the electrolyte solution where, e.g., the electrolyte solution is maintained in a relatively high-pressure environment.

In other embodiments, the temperature may be adjusted or allowed to change during the predetermined time period, e.g., within a range above the freezing point of the electrolyte solution and below the boiling point of the electrolyte solution.

As discussed previously herein, the temperature of the electrolyte solution may be controlled, e.g., maintained or adjusted, with the use of a temperature controlled vessel, e.g., a jacketed beaker, and a temperature sensor as described herein.

In some embodiments, the electrolyte solution may be mixed during the electrolysis, e.g., anodization process.

In some embodiments, the structure to be coated and/or surface-modified may be treated prior to the electrolysis, e.g., anodization process. For example, the structure to be coated and/or surface-modified may be electro-polished using methods known in the art prior to the electrolysis, e.g., anodization process. The structure to be coated and/or surface-modified may be subjected to one or more cleaning treatments (using, e.g., soap, acetone and/or ethanol) and/or ultrasound treatments, e.g., as described in the experimental section herein. In some embodiments, the structure to be coated and/or surface-modified may be subjected to an etching step, e.g., via plasma etching, prior to the electrolysis, e.g., anodization process.

Independently or in addition to one of the above pre-anodization treatment methods, structures having one or more microstructures or nanostructures, e.g., metal oxide nanotubes, formed thereon using the disclosed methods may be subjected to one or more post-anodization treatments, e.g., one or more ultrasound or electro-polishing treatments. Such post-anodization treatments may be desirable, for example, to remove surface debris (e.g., titania needles) remaining on the surface of the structure following anodization.

One or more steps of the methods disclosed herein may be computer controlled. For example, an electrical circuit including a power supply connected to the anode and the cathode or cathodes of the devices or systems disclosed herein may be under computer control. For example, such an electrical circuit may include a computer controlled relay to open and close the electrical circuit for the predetermined period of time. Where one or more temperatures sensors are present, such sensors may also be computer controlled. By integrating computer control of a temperature controlled jacketed beaker, a system can be provided which allows a user to program desired anodization conditions including time and temperature of the anodization. In this way, microstructures and/or nanostructures having desired dimensions and morphologies can be obtained on a variety of structures.

Suitable Materials for Coating

The structure to be coated and/or surface-modified, e.g., the structure including an electrically conductive surface may be made of (or coated with) a variety of suitable metal oxide producing metals, including, e.g., aluminum, niobium, tantalum, titanium, tungsten, zirconium and alloys including one or more of aluminum, niobium, tantalum, titanium, tungsten, zirconium.

In some embodiments, the structure to be coated and/or surface modified, e.g., the structure on which metal oxide nanotubes are to be formed, includes a metal, wherein the metal is present in the structure at a weight percent of least 0.1% relative to the total weight of the structure, e.g., at least 20 weight percent, at least 50 weight, or at least 90 weight percent. For example, in some embodiments, the metal may be present in the structure at a weight percent of from 0.1% to 100%, e.g., from 10% to 100%, from 20% to 100%, from 50% to 100%, or from 90% to 100% relative to the total weight of the structure.

A wide variety of structures may be coated or surface-modified using the devices, systems and methods disclosed herein. Structures of interest include structures having three-dimensional surfaces, e.g., complex three dimensional surfaces such as those found in many medical devices, e.g., medical implants such as microdevices, stents (e.g. cardiovascular stents, peripheral stents such as saphenous vein stents, cerebrovascular stents and coils), orthopedic implants and biosensors.

In some embodiments, a structure suitable as an object for coating and/or surface-modification using the devices, systems or methods disclosed herein may have a generally tubular shape, a generally cylindrical shape, a generally cuboid shape, a generally conical shape or a generally frustoconical shape.

Stents which may be coated and/or surface-modified using the devices, systems and methods disclosed herein include, for example, the R stent (OrbusNeich), Genous Bio-engineered R stent (OrbusNeich), BxVelocity stent (Cordis) Express2 stent (Boston Scientific), Blazer stent (OrbusNeich), Genous Bio-engineered Cobalt Chromium stent (OrbusNeich), Azule stent (OrbusNeich), SolarFlex & ChromoFlex stents (DISA Vascular), Driver stent (Medtronic), ML Vision stent (Abbott Laboratories), Coronnium stent (Sahajanand Medical technologies), Xience V™ stent (Abbott Laboratories), Taxus™ and Promus™ stents (Boston Scientific), and the Endeavor II™ (Medtronic).

Additional structures which may be coated and/or surface modified using the devices, systems and methods disclosed herein include, e.g., leadless pacemakers, arteiovenous shunts and fistulas, vascular/vein grafts, artificial coronary valves, and left atrial appendage closure devices.

In some embodiments, the devices, systems and methods disclosed herein find particular use in connection with the coating and/or surface-modification of medical devices for use in the cardiovascular space where a drug free method to induce reendothelialization, suppress vascular smooth muscle cell growth or provide an anti-inflammatory environment is required or desired.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., s or sec, second(s); min, minute(s); h or hr, hour(s); and the like.

Example 1

Coating of Titanium Stents with TiO$_2$ Nanotubes

TiO$_2$ nanotubes were formed on titanium stents and analyzed as set forth below.

Materials and Methods

Custom made titanium stents were acquired, which stents had a length of 15 mm and a diameter of 1.9 mm. Strut width and height was 100 μm. Prior to formation of the TiO$_2$ nanotubes, the stents were cleaned in three steps using soap, acetone and ethanol respectively (both electropolished and non-electropolished stents were utilized). At each step, an ultrasound treatment was performed for 5 min.

Figure 11:
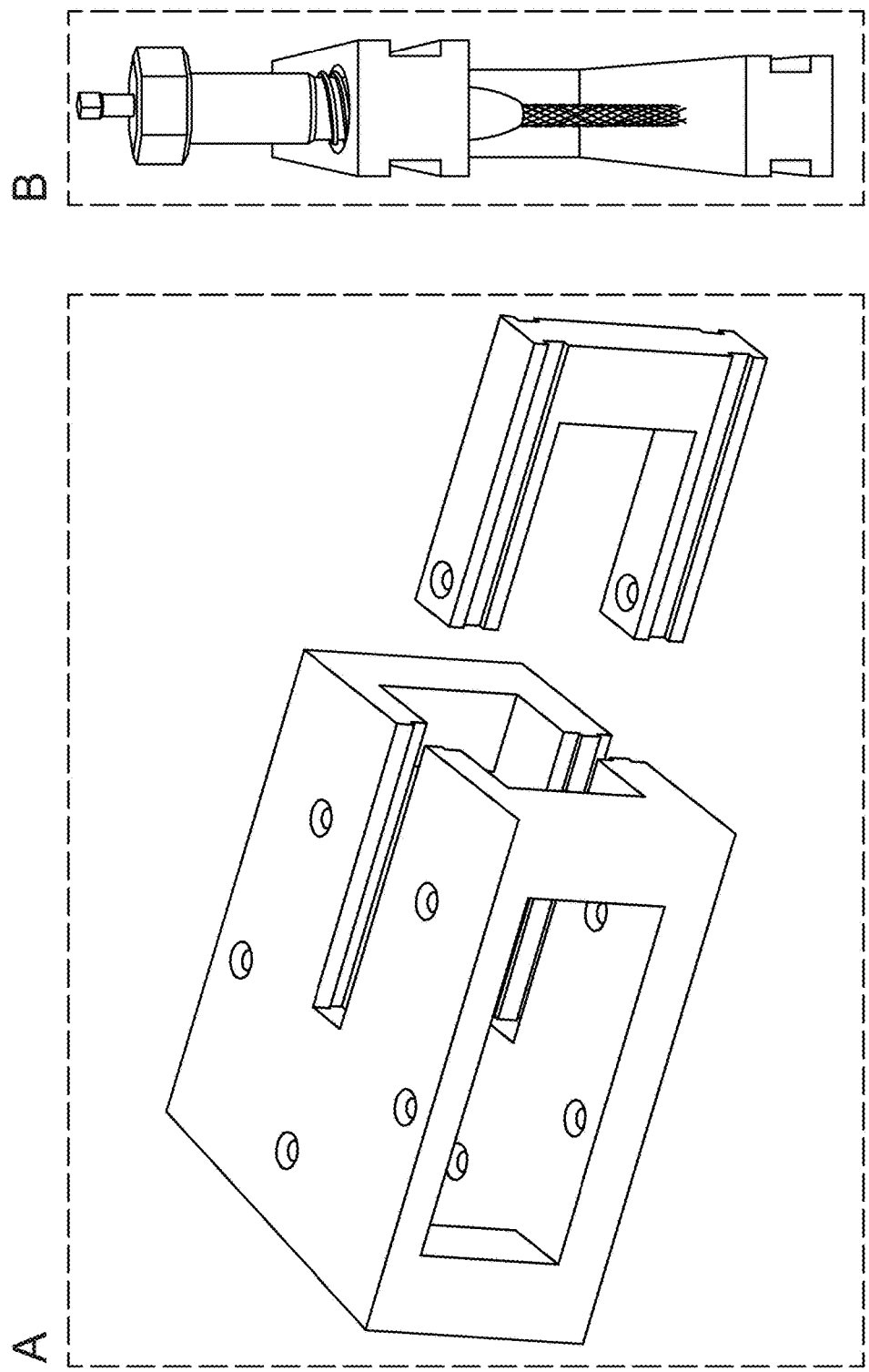
FIG. 11 shows an exemplary embodiment of a coating system according to the present disclosure, including a receiving frame and an inserter. Panel A shows the receiving frame and inserter without their corresponding cathodes and anode. Panel B shows the inserter with a stainless steel anode positioned in contact with a stent.

A first coating system, depicted generally in FIG. 11, panels A and B, was prepared which included a receiving frame with an anode receiving region. The receiving frame was assembled from individual acrylonitrile butadiene styrene (ABS) components prepared using a 3D printer. The receiving frame components included a first generally rectangular (top) plate, a second generally rectangular (bottom) plate, and four supports separating the first and second plates. Five platinum electrodes (cathodes), each with a diameter of 0.404 mm, were positioned in the receiving frame around the anode receiving region in a circular arrangement having a radius of 12.5 mm. An anode inserter, also prepared from ABS using the 3D printer, was configured with an opening into which an electrode in the form of a corrosion resistant, stainless steel screw (anode) was inserted. The stainless steel screw was configured to hold in place a stent and provide an electrical connection to the stent for anodization. The anode inserter, which was provided in a "C" shaped configuration, included a conically shaped projection as shown, for example, in FIG. 11, panel B. This conically shaped projection facilitated the positioning of the stent in the anode inserter between the anode and the conically shaped projection. The stainless steel screw provided an electrical connection between the stent and a power source. As shown in FIG. 11, panels A and B, the receiving frame was configured to removably receive the anode inserter via slide-fit engagement and thereby position the anode in the anode receiving region.

A second coating system was prepared which included a coating device including a first circular (top) plate defining an anode receiving opening and five cathode receiving openings positioned radially around the anode receiving opening. The second coating system also included a second circular (bottom) plate positioned in opposition to the first plate and including five cathode receiving openings. The second (bottom) plate also included a conically shaped projection as shown, for example, in FIG. 5. Two supports separated the first and second plates. Together the above structural elements provided a receiving region between the first and second plates. Five platinum electrodes (cathodes), each with a diameter of 0.404 mm, were positioned so that they extended through the five cathode receiving openings of the first plate and the five cathode receiving openings of the second plate. A stainless steel electrode (anode) was positioned to extend through the anode receiving opening in the first plate so as to contact a stent positioned in the receiving region. The first and second plates and the supports were prepared from ABS using a 3D printer.

Figure 9:
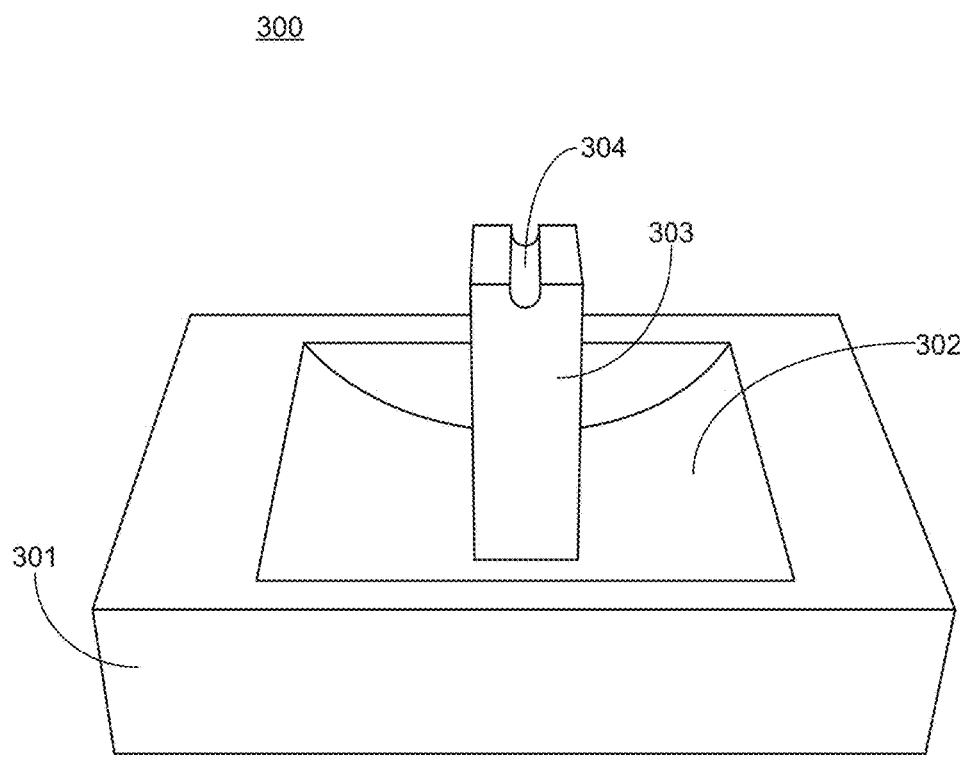
FIG. 9 shows an inserter configured for use with the coating device shown in FIGS. 5-8. The inserter includes an inserter arm adapted to hold a structure to be coated.
Figure 10:
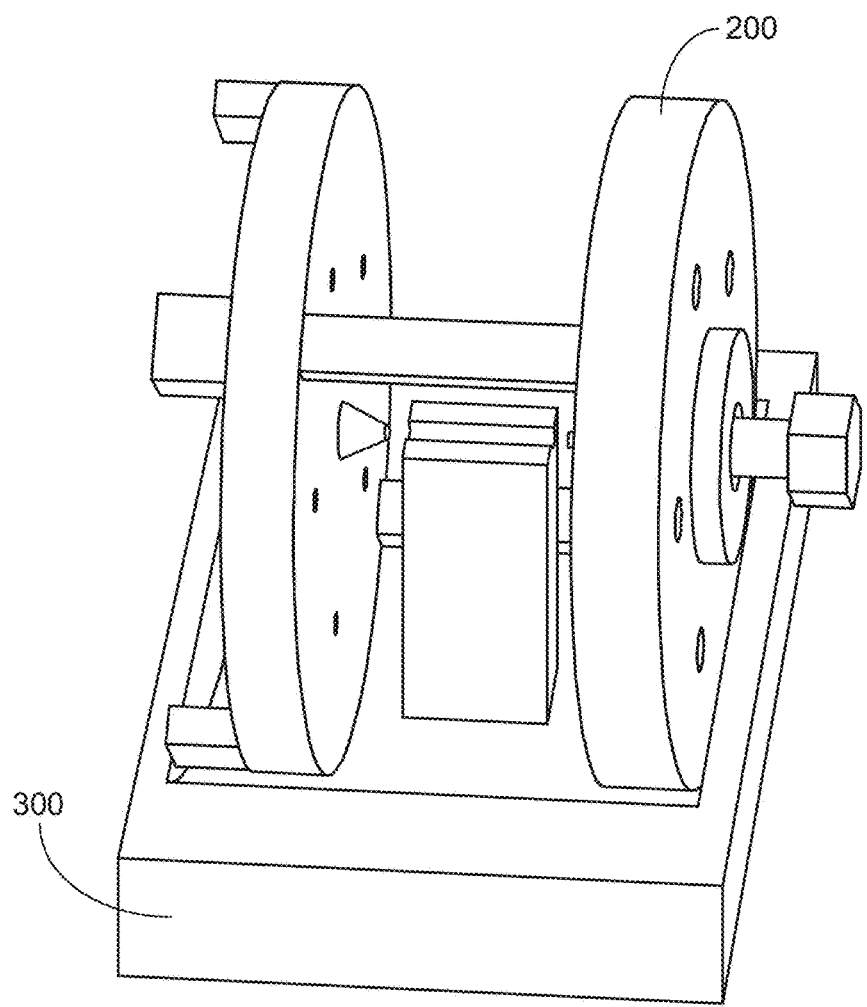
FIG. 10 shows the inserter shown in FIG. 9 slidably-engaged with the coating device shown in FIGS. 7 and 8 with the anode removed.

An inserter configured for insertion of the stent into the receiving region was also prepared from ABS using the 3D printer. The inserter was configured generally as shown in FIGS. 9 and 10 and included a base defining a curved cutout which was sized and shaped for slide-fit engagement with the external surfaces of the coating device. The inserter also included an inserter arm extending from the cut out portion. The inserter arm included a terminal groove which held the stent in place for insertion into the receiving region of the coating device. The stainless steel electrode (anode) provided an electrical connection between the stent and a power source.

The power supply was set up to provide a constant voltage between the cathodes and the anode during anodization, while the current was allowed to swing freely during anodization (usually in the range of mA). A computer controlled setup was built to open and close the electrical circuit, which allowed for the setting of synthesis times and monitoring of current and temperature (voltage was read from the power supply). The computer controlled set up was built using Tinkerforge™ modules (Tinkerforge GmbH, Römerstr. 18, 33758 Stukenbrock, Germany) and the software was written in Python™ code.

Prior to anodization using the first coating system, the anode inserter was utilized to insert a stent into the anode receiving region of the receiving frame. The receiving frame was placed in an electrolyte solution of ethylene glycol, water and ammonium fluoride at a ratio of (9:1:3 g/L). Nanotube synthesis was then performed over a time period of from 5 to 90 minutes at room temperature (RT) using a constant voltage of from 15V to 110 V. After nanotube synthesis, the stents were rinsed using ethanol and debris was removed using ultrasound, while immersed in ethanol (5-30 min). The stents were then stored at RT and atmospheric pressure in ethanol or phosphate buffer (pH 7.4). The stents were analyzed using electron microscopy which was performed using a Carl Zeiss Ultra 55 Field Emission Scanning Electron Microscope.

Results

Figure 12:
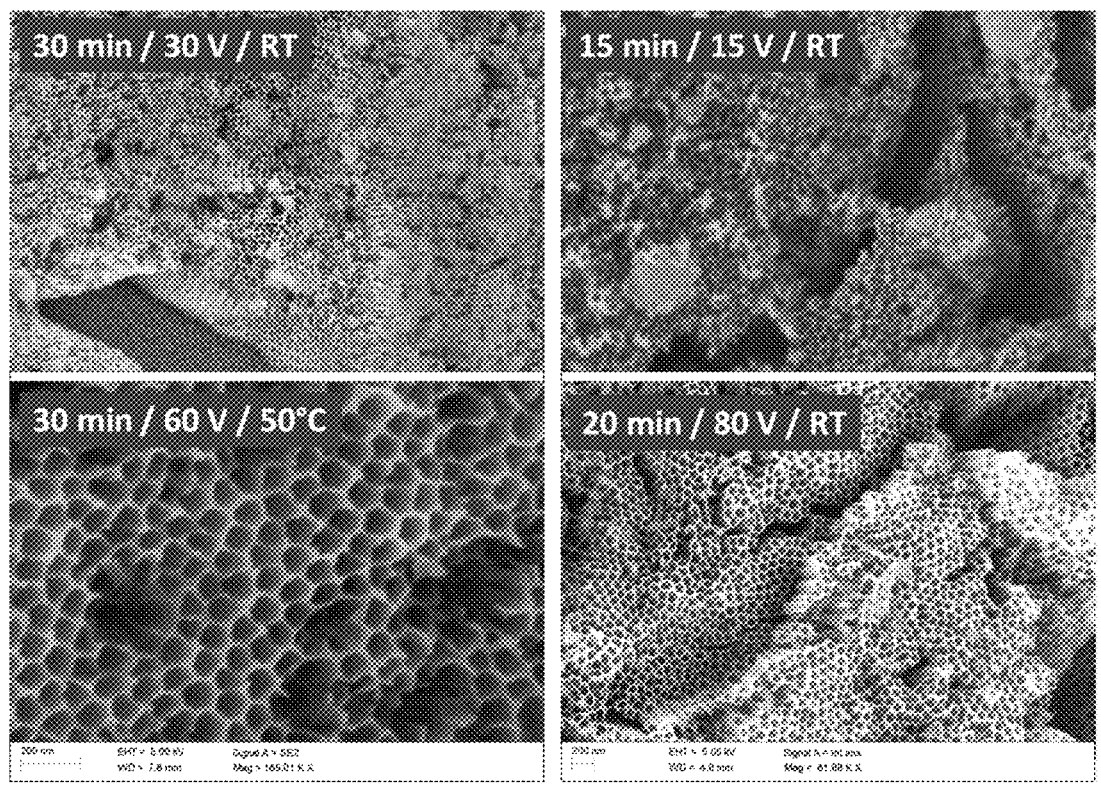
FIG. 12 shows Scanning Electron Microscope (SEM) images of $TiO_2$ nanotube-coated stents formed using various parameters (top left—anodization at 30 V and RT for 30 min), (top right—anodization at 15 V and RT for 15 min), (bottom left—anodization at 60 V and 50° C. for 30 min), and (bottom right—anodization at 80 V and RT for 20 min).

Table 1 (below) and FIG. 12 show exemplary results from the nanotube synthesis reactions.

TABLE 1

| Reaction time [min] @ V | Length [μm] | Diameter [nm] |
|---|---|---|
| 15 @ 60 V | 1.2 ± 0.2 | 40 |
| 30 @ 60 V | 2.5 ± 0.3 | 110 |
| 60 @ 60 V | 6.5 ± 0.3 | 110 |
| 15 @ 30 V | 2.0 ± 0.3 | 50 |
| 15 @ 45 V | 0.9 ± 0.1 | 55 |
| 15 @ 90 V | Multi-layered | 110 |
| 15 @ 110 V | Multi-layered | 140 |
| 20 @ 30 V | 1.8 ± 0.3 | 50 |
| 20 @ 60 V | 7.5 ± 0.3 | 80 |
| 20 @ 80 V | 8.0 ± 0.4 | 110 |

As shown in Table 1, stents having titanium dioxide nanotube layers wherein the titanium dioxide nanotubes had an average length from about 1.2 μm to about 8 μm and an average diameter of from about 40 nm to about 140 nm were obtained using the parameters set forth above. FIG. 12 shows SEM images demonstrating the successful formation of $TiO_2$ nanotubes on stents using the indicated parameters and provides examples of different nanotube dimensions that have been obtained using different parameters.

Example 2

Coating Stability and Characterization of $TiO_2$ Nanotube-Coated Stents

The stability of the $TiO_2$ nanotube layer was tested under compression and expansion conditions as set forth below.

Materials and Methods

Stents with $TiO_2$ nanotubes coated thereon were crimped onto balloon catheters (15×3.5 or 15×2.5 mm; Creganna-Tactx Medical) using a bench top manual stent crimping device (Machine Solutions, Inc.). The surface-modified stents were compressed to 1.2 mm for 30 s. Subsequently, the stents were inflated to 3.5 mm and 2.5 mm using the corresponding balloons at a pressure of 10 atm for 30 s as indicated by the manufacturer.

Results

Figure 13:
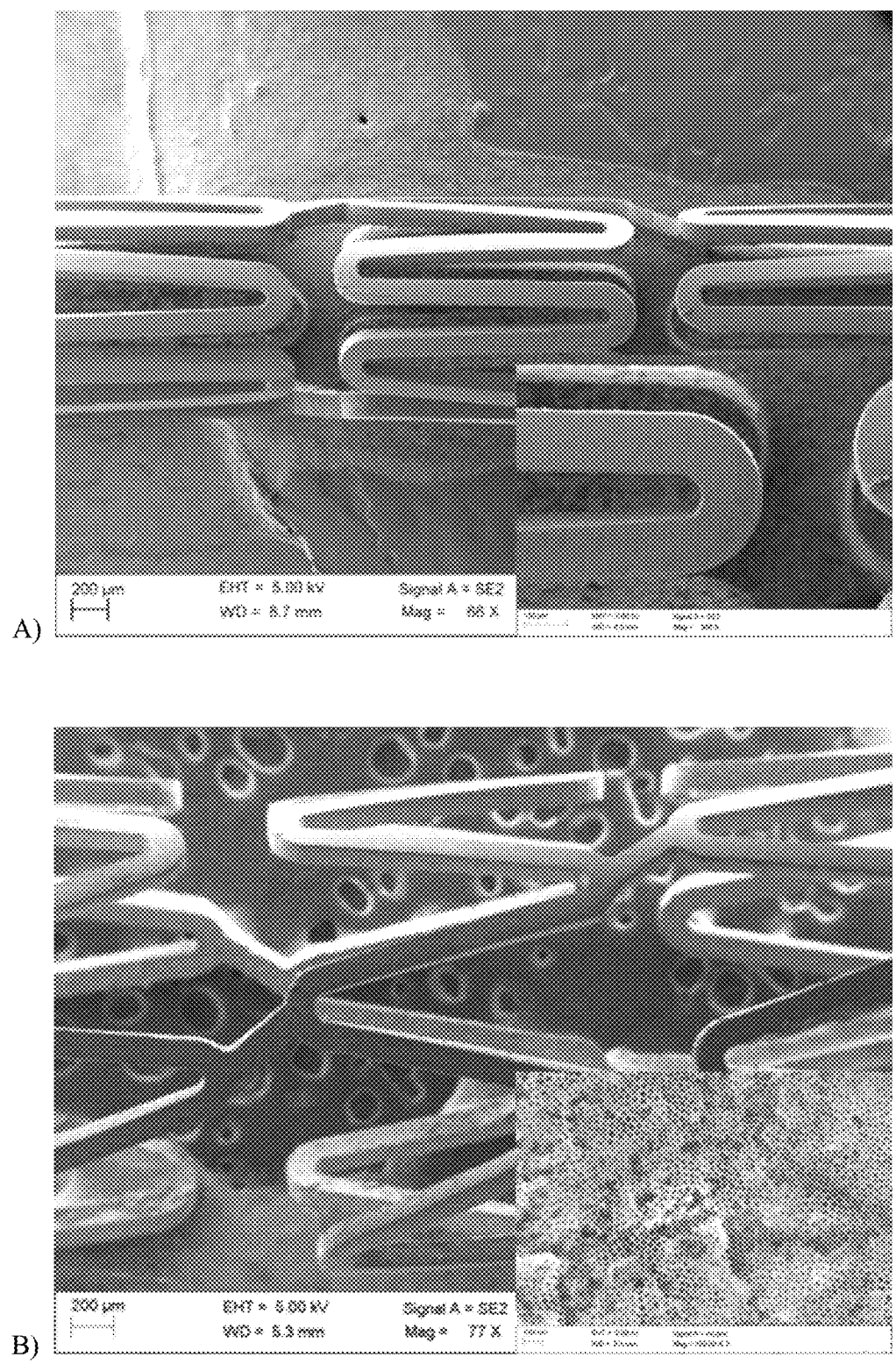
FIG. 13 shows SEM images of a A) crimped and B) inflated stent. A) The $TiO_2$ nanotube coating remains intact after compression from the stents initial diameter (1.8 mm) to 1.2 mm (compression time: 30 s). B) The same stent was inflated to 2.5 mm using a 2.5×15 mm delivery balloon catheter and a pressure of 10 atm for 30 s as indicated by the manufacturer. The inserts show that the coating remained intact and the nanotubular array was not distorted.

Following compression and expansion as indicated above the $TiO_2$ nanotube layer or layers remained largely intact with >80% of the layer or layers remaining intact following expansion to 3.5 mm and >95% of the layer or layers remaining intact following expansion to 2.5 mm. SEM images of an exemplary compressed and inflated stent are provided in FIG. 13. In panel A, the $TiO_2$ layer remains intact after compression from the stent's initial diameter (1.8 mm) to 1.2 mm (compression time: 30 s). Panel B shows an image of the same stent inflated to 2.5 mm using a 2.5×15 mm delivery balloon catheter at a pressure of 10 atm for 30 s, as indicated by manufacturer. The image inserts show that the $TiO_2$ layer remains intact and the nanotubular array is not distorted.

Example 3

Mechanical Stability of $TiO_2$ Nanotube-Coated Stents

During anodization a portion of the substrate is converted into nanotubes thereby reducing the thickness of the substrate. Accordingly, there is a risk that the mechanical properties of the stent may be altered as a result of the anodization process. The mechanical properties of the $TiO_2$ nanotube-modified stents were tested as indicated below.

Materials and Methods

Hoop force measurements were conducted on surface-modified and unmodified stents. Compression speed was set to 94.34 μm/s, and the stents were compressed from a diameter of 2.3 mm down to a final diameter of 0.81 mm. A plateau in the Hoop force was reached at 1.2 mm. Further compression beyond this point resulted in an increase in the Hoop force due to the struts of the stent coming into contact with each other, which resulted in damage to the $TiO_2$ layer.

Results

Figure 14:
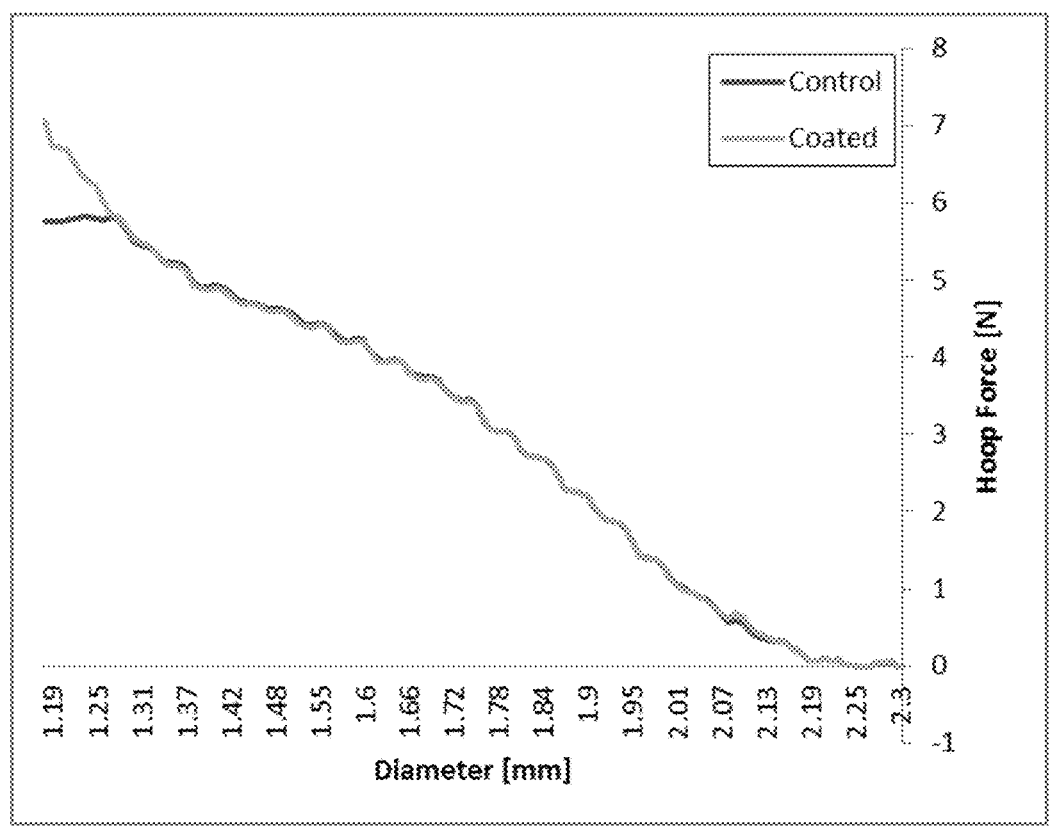
FIG. 14 provides a graph showing Hoop force relative to diameter for a coated and non-coated stent. No significant difference in the compression force over the relevant diameter (1.9 to 1.2 mm) was detected demonstrating that the mechanical properties of the stents, as indicated by Hoop force, were not altered during anodization. The compression speed for the Hoop force measurements was 94.34 µm/s.

Over the relevant range of 1.9 mm to 1.2 mm there was no significant difference in the recorded Hoop force for coated and uncoated stents. This result, illustrated in FIG. 14 demonstrates that the mechanical properties of the stent, as determined by Hoop force measurements, are not altered during anodization.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of forming metal oxide nanotubes uniformly on a three dimensional surface of a structure, the method comprising:
   positioning a single structure in a coating device comprising:

a first plate comprising a central anode receiving opening and at least three cathode receiving openings positioned radially around the central anode receiving opening;
a second plate positioned in opposition to the first plate and comprising at least three cathode receiving openings;
a plurality of supports separating the first and second plates,
the at least three cathodes extending through the at least three cathode receiving openings of the first plate and into the at least three cathode receiving openings of the second plate; and
the anode extending through the central anode receiving opening and contacting the structure and positioning the structure in the centrally positioned receiving region relative to at least three cathodes, wherein the structure comprises a metal and the metal is at least 0.1 weight percent of the structure and wherein the structure is positioned at an equal distance from each of the at least three cathodes,
wherein the anode holds the structure in place and electrically connects the structure to a power source and wherein the at least three cathodes are separate individual cathodes;
submerging the structure and the at least three cathodes in an electrolyte solution; and
applying electrical energy between the anode and the at least three cathodes for a period of time sufficient to form metal oxide nanotubes on the three dimensional surface of the structure,
wherein the method provides for uniform growth of the metal oxide nanotubes on the three dimensional surface of the structure.

2. The method of claim 1, wherein the nanotube comprises an oxide of the metal.

3. The method of claim 1, wherein the oxide of the metal is a metal oxide comprising an oxide of aluminum, niobium, tantalum, titanium, tungsten, zirconium or mixtures thereof.

4. The method of claim 1, wherein the metal is at least 10 weight percent of the structure.

5. The method of claim 1, wherein the period of time is sufficient to form at least one nanotube with a length of at least 10 nm on the three dimensional surface of the structure.

6. The method of claim 1, wherein the diameter of the at least one nanotube is a diameter in the range of from 1 nm to 1,000 nm.

7. The method of claim 1, wherein the diameter of the at least one nanotube is a diameter in the range of from 10 nm to 200 nm.

8. The method of claim 1, wherein the step of applying electrical energy between the anode and the at least three cathodes comprises applying a substantially constant voltage for the period of time ranging from 5 minutes to 90 minutes.

9. The method of claim 8, wherein the substantially constant voltage is a substantially constant voltage in the range of from about 10 Volt to 100 kilovolts.

10. The method of claim 1, wherein the step of applying electrical energy between the anode and the at least three cathodes comprises applying a substantially constant current for the period of time.

11. The method of claim 10, wherein the substantially constant current is a substantially constant current in the range of from about 1 femtoampere to about 100 kiloamperes.

12. The method of claim 1, wherein the electrolyte solution comprises compounds of aluminum, niobium, tantalum, titanium, tungsten, zirconium or mixtures thereof.

13. The method of claim 1, wherein the structure comprises a medical device or a portion thereof.

14. The method of claim 13, wherein the medical device comprises a stent, sensor, arteriovenous shunt, pacemaker, or combinations thereof.

15. The method of claim 1, wherein the method comprises maintaining the electrolyte solution at a substantially constant temperature.

16. The method of claim 15, wherein the substantially constant temperature is above a freezing point of the electrolyte solution and below a boiling point of the electrolyte solution.

17. The method of claim 16, wherein the substantially constant temperature is a substantially constant temperature in the range of from about 10° C. to about 50° C.

18. The method of claim 1, wherein the period of time is a time in the range of from 5 seconds to 5 days.

19. The method of claim 18, wherein the period of time is a time in the range of from 10 min to 60 min.

20. The method of claim 1, wherein the structure is electropolished prior to the submerging in the electrolyte solution.

21. The method of claim 1, wherein the one or more cathodes comprise aluminum, niobium, tantalum, titanium, tungsten, zirconium or alloys thereof.

22. The method of claim 1, wherein the one or more cathodes comprise graphite.

23. The method of claim 1, wherein the second plate includes a projection and wherein the structure is held in place by the anode and the projection.

24. The method of claim 1, wherein the device comprises at least five cathodes and wherein the first plate comprises at least five cathode receiving openings positioned radially around the central anode receiving opening and the second plate comprises at least five cathode receiving openings and the structure is positioned at an equal distance from each of the at least five cathodes.

* * * * *